US005856178A

United States Patent [19]
White et al.

[11] Patent Number: 5,856,178
[45] Date of Patent: *Jan. 5, 1999

[54] DNA CASSETTES FOR EXPRESSION OF LYTIC PEPTIDES IN MAMMALIAN CELLS AND TRANSGENIC ORGANISMS CONTAINING SAME

[75] Inventors: Kenneth L. White; John Morrey, both of N. Logan; William A. Reed, Benson, all of Utah

[73] Assignee: Utah State University, North Logan, Utah

[*] Notice: The term of this patent shall not extend beyond the expiration date of Pat. No. 5,548,075.

[21] Appl. No.: 723,306

[22] Filed: Sep. 30, 1996

Related U.S. Application Data

[60] Division of Ser. No. 480,454, Jun. 7, 1995, abandoned, which is a continuation-in-part of Ser. No. 114,692, Aug. 30, 1993, Pat. No. 5,548,075.

[51] Int. Cl.$^6$ .................. C12N 15/79; C12N 15/63; C12N 15/09
[52] U.S. Cl. .................. 435/302.1; 435/375; 435/69.1; 435/6; 435/172.3
[58] Field of Search .................. 435/320.1, 375, 435/69.1, 172.3, 6

[56] References Cited

U.S. PATENT DOCUMENTS

| | | |
|---|---|---|
| 4,507,230 | 3/1985 | Tam et al. . |
| 4,873,316 | 10/1989 | Meade et al. . |
| 4,952,499 | 8/1990 | Cantor et al. . |
| 4,992,367 | 2/1991 | Cullen . |
| 5,045,531 | 9/1991 | Berkowitz et al. . |
| 5,096,886 | 3/1992 | Boman et al. . |
| 5,166,321 | 11/1992 | Lai et al. . |
| 5,215,904 | 6/1993 | Gould et al. . |
| 5,227,301 | 7/1993 | Turner et al. . |
| 5,304,489 | 4/1994 | Rosen . |
| 5,320,952 | 6/1994 | Deutch et al. . |
| 5,322,775 | 6/1994 | Clark et al. . |
| 5,344,765 | 9/1994 | Lai et al. . |
| 5,357,044 | 10/1994 | Lai et al. . |
| 5,366,894 | 11/1994 | Clark et al. . |
| 5,556,782 | 9/1996 | Cooper et al. ............ 435/240.2 |

FOREIGN PATENT DOCUMENTS

| | | |
|---|---|---|
| 0 264 166 | 4/1988 | European Pat. Off. . |
| 2 223 755 A | 4/1990 | United Kingdom . |
| WO 88/01648 | 3/1988 | WIPO . |
| WO 89/00194 | 1/1989 | WIPO . |
| WO 89/04371 | 5/1989 | WIPO . |
| WO 89/00199 | 12/1989 | WIPO . |
| WO 90/03432 | 4/1990 | WIPO . |
| WO 90/05188 | 5/1990 | WIPO . |
| WO 90/12866 | 11/1990 | WIPO . |
| WO 91/08216 | 6/1991 | WIPO . |
| WO 93/04165 | 3/1993 | WIPO . |
| WO 93/24138 | 12/1993 | WIPO . |
| WO 93/25567 | 12/1993 | WIPO . |
| WO 94/05796 | 3/1994 | WIPO . |
| WO 94/04688 | 4/1994 | WIPO . |
| WO 94/15961 | 7/1994 | WIPO . |
| WO 94/16570 | 8/1994 | WIPO . |

OTHER PUBLICATIONS

Altiok et al., "Interaction of two sequence-specific single-stranded DNA-binding proteins with an essential region of the beta-casein gene promoter is regulated by lactogenic hormones", *Molecular and Cellular Biology*, vol. 13, No. 12, pp. 7303–7310, Dec. 1993.

Ashktroab et al., "Bovine beta-casein (BBC) gene promoter activity and hormonal induction (HI) of its expression in mammary epithelial cell (MEC) line", *FASEB Journal*, vol. 9, No. 3, p. A83, abstract no. 490, Mar. 1995.

Jaynes et al., "Expression of a Cecropin B lytic peptide analog in transgenic tobacco confer enhanced resistance tobacterial wilt caused by *Pseudomonas solanacearum*", *Plant Science*, vol. 89, pp. 43–53, 1993.

Mercier et al., "Structure and function of milk protein genes", *Journal of Dairy Science*, vol. 76, No. 10, pp. 3079–3098, 1993.

Novak et al., "Regulatory anatomy of the murine interleukin-2 gene", *Nucleic Acids Research*, vol. 18, No. 15, pp. 4523–4533, 1990.

J. Jaynes et al., "In Vitro Cytocidal Effect of Novel Lytic Peptides on Plasmodium falciparum and Trypansoma cruzi," *FASEB J.*, 2:2878–2883 (1988).

W. Reed et al., "Enhanced In Vitro Growth of Murine Fibroblast Cells and Preimplantation Embryos Cultured in Medium Supplemented with an Amphipathic Peptide," *Mol Reprod & Devel*, 31: 106–113 (1992).

Kappel et al. "Regulating gene expression in transgenic animals," Current Opinion in Biotechnology, vol. 3: 548–553, 1992.

*Primary Examiner*—Jasemine C. Chambers
*Assistant Examiner*—Karen M. Hauda
*Attorney, Agent, or Firm*—Trask, Britt & Rossa

[57] ABSTRACT

Expression cassettes for expression of amphipathic (lytic) peptides in mammalian unicellular (e.g., cultured cells) and multicellular organisms are described, as well as transgenic unicellular and multicellular mammalian organisms having such a cassette stably integrated in their genetic material. In one embodiment, the expression cassette comprises a milk-specific promoter, which for example may be the beta casein promoter, linked in reading frame to control the expression of an amphipathic peptide encoding gene. This expression cassette is useful for production of amphipathic peptides in milk-producing cells and tissues. In another embodiment, the expression cassette comprises an interleukin regulatory sequence adjacently linked to control the expression of an amphipathic peptide encoding gene. The interleukin-regulated cassette is useful to produce disease-resistant animals.

13 Claims, 5 Drawing Sheets

DNA CASSETTES FOR EXPRESSION OF LYTIC PEPTIDES IN MAMMALIAN CELLS AND TRANSGENIC ORGANISMS CONTAINING SAME

This is a divisional patent application of U.S. Ser. No. 08/480,454, filed Jun. 7, 1995, abandoned, which is a continuation-in-part of U.S. Ser. No. 08/114,692, filed Aug. 30, 1993, issued as U.S. Pat. No. 5,548,075.

BACKGROUND OF THE INVENTION

1. Field of the Invention

The invention is directed to transgenic expression of amphipathic and lytic peptides in mammalian organisms, and particularly to transgenic mammalian unicellular and multicellular organisms having stably-integrated amphiphathic peptide-encoding genes whose expression is controlled by a tissue-specific mammalian regulatory sequence.

2. State of the Art

A class of cellular polypeptides known as "lytic peptides" or "amphipathic peptides" has been found to be active against various disease-causing agents including bacteria and viruses. These amphipathic peptides form complexes in the cell's outer coat or membrane, and a present hypothesis is that the complexes form pores which allow unregulated transfer of fluid and molecules across the membrane. According to this hypothesis, the cells die because of osmotic imbalances resulting from this unregulated transfer. Whatever the mechanism, the naturally occurring amphipathic peptides and various modified peptides having certain peptide sequence or structure in common with the naturally occurring amphipathic peptides have been found to have cytocidal activity against bacteria, fungi, protozoans, and various other microbial pathogens.

PCT patent publication No. WO 89/00194 (priority date U.S. patent application filed Jul. 7, 1987), by Jaynes et al., discloses numerous amphipathic peptides including both naturally occurring ones and modified amphipathic peptides. An earlier application by Jaynes et al., U.S. Pat. application Ser. No. 07/889,225 filed Jul. 25, 1986, discloses vectors encoding certain amphipathic peptides and the production of disease-resistant transgenic plants containing gene sequences expressing such amphipathic peptides. The Jaynes applications also disclose use of amphipathic peptides for injection or application to a sick organism.

Quantities of amphipathic peptides or amphipathic peptide analogues sufficient for experimental use can be made on a peptide synthesizer. However, this method is not suitable for commercial production or even for amounts needed for clinical trials of amphipathic peptides as disease-treating agents.

Attempts have been made to produce amphipathic peptides by overproduction in various host species. Amphipathic peptides can be produced in insect cell cultures using the baculovirus-Spodoptera expression system, as the amphipathic peptides are native to these insect species and the insect cells are somewhat resistant to their toxic effects. Efforts to express amphipathic peptides in non-insect hosts have generally worked poorly, because of the toxic effects of the amphipathic peptides on the host cells or organisms. While Jaynes et al. were able to produce transgenic plants expressing an amphipathic peptide, their success is due to the difference in cell wall and membrane structures of plants, which render them insusceptible to attack by the amphipathic peptide. So far as the present inventors are aware, the only successful production of a transgenic mammalian organism containing an expressible lytic peptide gene is that disclosed in the related copending application Ser. No. 08/114,692 of White and Reed. These inventors were able to produce transgenic mice and transformed lymphocytes carrying an integrated lytic peptide-encoding gene under the control of an interleukin regulating sequence. However, these organisms were not particularly suited for achieving large-scale production of amphipathic peptides.

Further, the production of novel organisms by techniques of genetic engineering, including both unicellular and multicellular organisms and tissue culture cell lines, has been applied to achieve various objectives. For example, the "Harvard mouse" is a strain of mice which have been genetically altered to have increased susceptibility to the induction of cancer by damaging to a particular gene. Another example is the development of a bacterial strain carrying a foreign gene which confers the ability to "eat" petroleum and related compounds on the host.

Desirably, in a genetically-engineered organism, the foreign gene should be stably present in the germ cells of the organism so that it is transmitted to its offspring and to subsequent generations of the organism. Further, it is often desirable that the process of obtaining the transgenic organism not require integration of the gene at a specific site in order for expression of the gene to occur. This makes the process more reproducible, which is particularly important when dealing with alteration of multicellular animals where the generation times are generally long compared to those of unicellular organisms.

However, so far as the present inventors are aware, no one has yet been able to achieve a disease-resistant mammalian or other non-insect vertebrate unicellular or multicellular organism, having an expressible gene encoding an amphipathic peptidestably integrated into its genome. While Jaynes et al. were able to produce transgenic plants expressing an amphipathicpeptide, their success may be due to the difference in cell structure of plants, such as the cell wall and membrane structures, which make them insusceptible to attack by the amphipathic peptide. In contrast, in other prokaryotic and non-insect eukaryotic cells and animals, expression of an introduced gene for an amphipathic peptide can result in death or serious harm to the host cell. If the gene encoding the amphipathic peptide is under the control of a regulator that permits even low levels of expression, long-term growth of the host (or culture of the cell line) is difficult to achieve.

While their sensitivity is less than that of bacteria and most eukaryotic pathogens, mammalian cells are also susceptible to killing by amphipathic peptides. Unless the gene encoding the amphipathic peptide is under very tight control, leaky expression of the peptide has generally negative effects on host mammalian cells. However, if tight control is provided, one is faced with the problem of how to obtain selective and beneficial expression of the amphipathic peptide, otherwise the benefits of the integrated gene cannot be realized.

So far as the present inventors are aware, to date there have been no successful attempts to selectively express amphipathic peptides in a beneficial manner in particular mammalian cell types or tissues. Accordingly, a need remains for means to achieve such selective expression of amphipathic peptides in mammalian cells and organisms.

Nor are the inventors aware of any successful attempts to use a non-insect expression system, or a transgenic mammalian peptide expression system, for production of amphipathic peptides in large quantity. Accordingly, a need also remains for means to produce amphipathic peptides in large quantities.

Further, a need remains for a DNA cassette and method for producing mammalian and non-insect eukaryotic transgenic organisms having a stably integrated gene encoding an amphipathic peptide, with the gene being selectively expressed only under conditions such as disease states where expression is desirable and without significantly jeopardizing the general hardiness and well-being of the host organisms. A need further remains for such DNA cassette and method which is useful to transfect both unicellular and multicellular non-insect vertebrate organisms.

SUMMARY

The invention comprises expression cassettes for amphipathic peptides in mammalian unicellular (e.g., cultured cells) and multicellular organisms, as well as transgenic unicellular and multicellular mammalian organisms having such a cassette or cassettes stably integrated in their genetic material.

In one embodiment, the invention comprises an expression cassette for production of amphipathic peptides in milk-producing cells and tissues, and transgenic unicellular and multicellular organisms containing the cassettes. The expression cassette comprises a milk-specific promoter, which for example may be the beta casein promoter, linked in reading frame to control the expression of an amphipathic peptide encoding gene. The invention further embraces organisms producing amphipathic peptides via expression of the cassettes, and amphipathic peptides produced by such organisms.

In a preferred embodiment for milk production of amphipathic peptides, the amphipathic peptide is produced as a fusion protein wherein the fusion peptide renders the amphipathic peptide harmless to the cell. After secretion in milk, the fusion peptide is readily cleaved from the fusion protein to yield the free amphipathic peptide. Further desirably, the fusion peptide may be a marker peptide which serves for detection and/or isolation of the fusion protein from milk.

A method of producing an amphipathic peptide comprises the steps of providing a cassette comprising promoter segment encoding a 5' promoter region which normally cis-regulates expression of a native milk-specific protein-encoding gene, linked upstream to regulate the expression of a segment encoding an amphipathic peptide; stably integrating the cassette into the genome of a milk-producing mammalian organism; collecting milk produced by the mammalian organism; and purifying the amphipathic peptide from the collected milk. In an alternate embodiment of the method, the organism is a mammalian cell line in culture which is capable of producing a milk protein under the regulation of the 5' promoter region, such as the HC11cell line which produces beta casein, and the method further includes a step of treating the cells having the integrated cassette with lactogenic hormones to activate the 5' promoter region. Methods of producing transgenic organisms carrying the cassette having the 5' promoter region regulating expression of amphipathic peptide are also provided.

In an alternate embodiment, the invention provides a DNA cassette comprising a sequence encoding an amphipathic peptide under the transcriptional control of regulating sequences that normally permit expression only when a defined indicator(s) reflective of a disease state is present, and which tightly inhibit expression when such indicator(s) is absent. Presently preferred embodiments use interleukin regulatory sequences, especially the regulatory sequences of interleukin-2 or interleukin-12. In a further preferred embodiment of multicellular organisms, the cassette is incorporated into the genomes of the germ cells and the organisms are capable of transmitting it to their offspring, to enable production of disease-resistant animals.

In another preferred embodiment, the cassette is incorporated into cells such as tumor-infiltrating lymphocytes or bone marrow stem cells removed from a host for transfection, and then re-introduced into the patient to provide therapeutic benefits.

Desirably, the encoded amphipathic peptide is one which is more toxic to selected target pathogens than to the mammalian or non-insect vertebrate host cells. In a presently preferred embodiment, the encoded amphipathic peptide is Shiva-1. However, other useful amphipathic peptides and modified amphipathic peptides include cecropin-B, SB-37, Anubis-1, -2, -3 and -4; Shiva-2, -3, -4, -5, -6, -7, -8, -9 and -10; melittin; Hecate-1, -2, and -3; Manitou-1; AP-1; and Vishnu series amphipathic peptides.

The unicellular organisms of the invention include mammalian tissue culture cells, embryonic stem cells useful for producing transgenic animals carrying the cassette, and cells removed from a mammalian host for temporary culture in vitro, such as bone marrow cells or tumor-infiltrating lymphocytes (TILs), prior to reintroduction into the host.

It is within contemplation that other regulating sequences may be useful in the DNA cassette. Suitable sequences would control expression of the amphipathic peptide such that it is expressed in tandem with a host's normal response to a disease condition, and is not "leaky" under normal conditions, e.g. there is little or no production of the amphipathic peptide in the absence of a disease state recognizable by the host organism. Sequences which may be useful include c-myc-regulating sequences and tumor necrosis factor-regulating sequences.

The invention further embraces methods of making the transgenic animals and cells, and methods of using cells carrying the cassette.

DETAILED DESCRIPTION OF THE ILLUSTRATED EMBODIMENT

Figure 1:
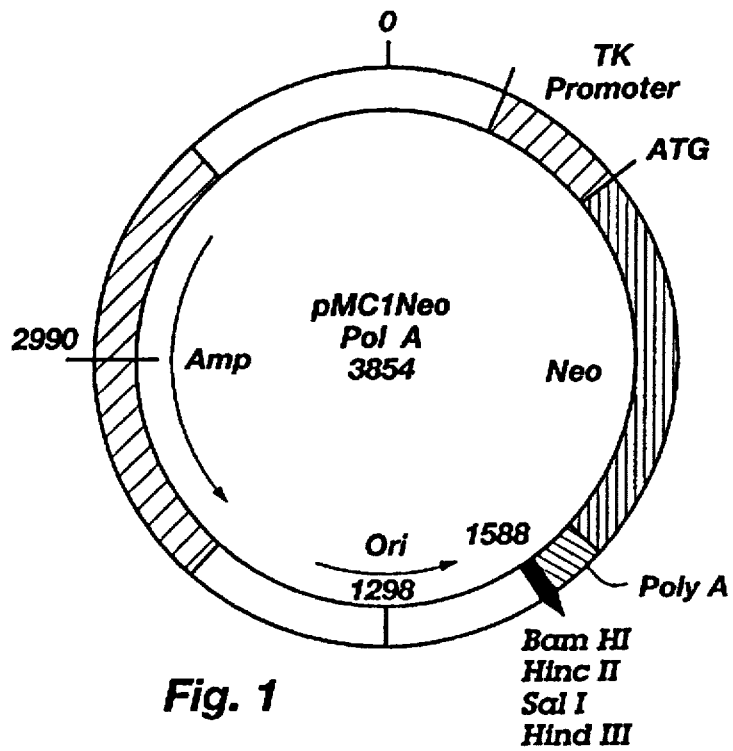
FIG. 1 depicts a general map of a commercially available plasmid carrying a NEO expression cassette useful to make the cassette of one embodiment of the invention.
Figure 2:
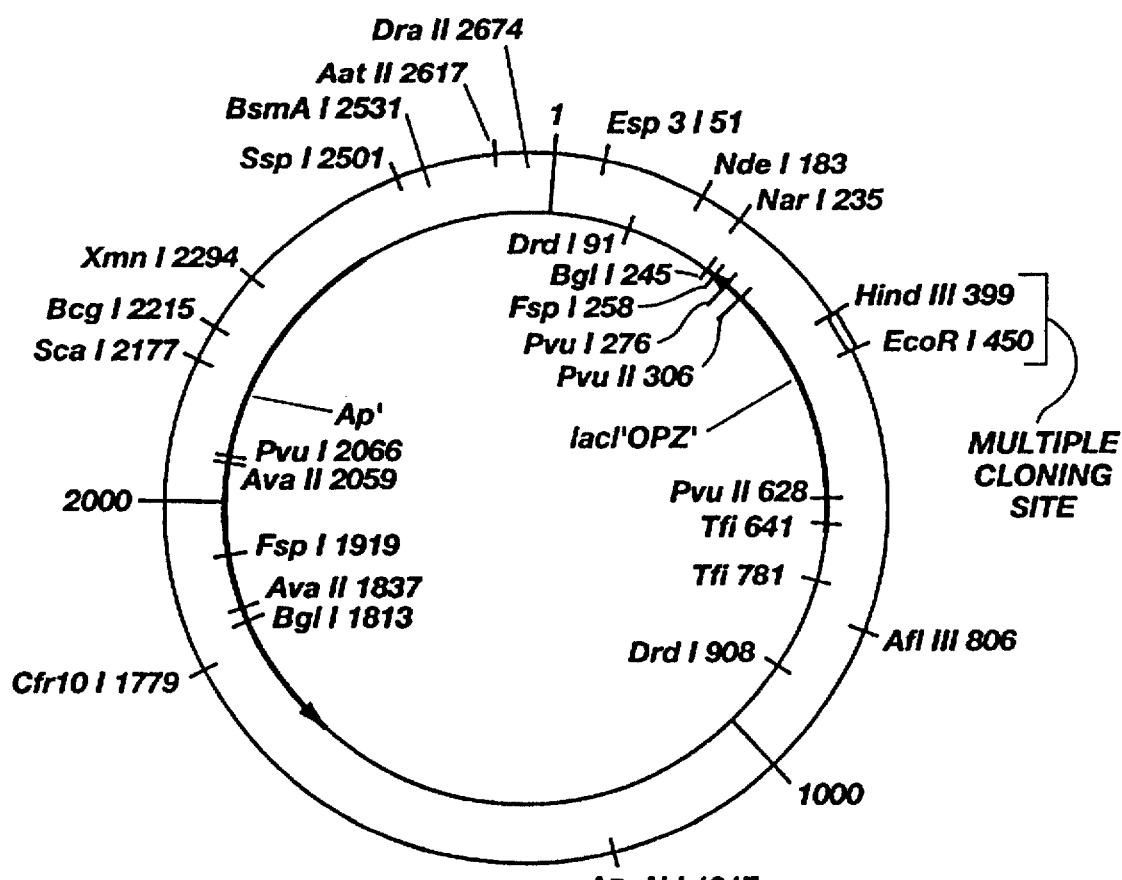
FIG. 2 depicts a general map of another plasmid used as a basis for a cassette of the invention.

In an embodiment presently preferred for production of amphipathic peptides in milk, the cassette comprises a milk-specific protein 5' regulatory sequence placed upstream of, and in reading frame with, a gene encoding an amphipathic peptide. The 5' regulatory sequence is derived from the 5' region of a native milk-specific protein-encoding gene. In a further embodiment, the cassette includes a 3' regulatory sequence from a native milk-specific protein gene, the 3' regulatory sequence being located downstream from the amphipathic peptide-encoding gene. The 3' regulatory segment includes a polyadenylation signal, and may also include a stop codon if none is present in the amphipathic peptide-encoding gene. In embodiments lacking the 3' milk-specific protein regulatory segment, the cassette should include a polyadenylation signal region derived from another source such as SV-40.

In an illustrated embodiment (SEQ ID No. 6), the 5' regulatory sequence is derived from a *Bos taurus* beta casein genomic clone GENBANK accession # M14711 using the primers of SEQ ID Nos. 7–8, with the 3' regulatory sequence from the pGFP-C1 plasmid (commercially available from CLONTECH Laboratories, 4030 Fabian Way, Palo Alto, Calif. 94303) added starting with residue 8798. Another, presently preferred embodiment (SEQ ID No. 5) combines the 5' beta casein promoter with a 3' beta casein regulatory sequence including a polyadenylation signal, the 3' sequence being obtained using the primers of SEQ ID Nos. 9–10 from the genomic clone.

While the milk-specific promoter is exemplified in SEQ ID Nos. 5 and 6 as being the beta casein promoter, a number of other milk-specific promoters could be substituted. These include at least portions of the regions specified in Table I, of various such promoters whose GENBANK accession numbers are given. Provided that the promoter is inserted in the proper reading frame as shown in the examples here given, cassettes having an amphipathic peptide under the control of any of the milk-specific promoters listed in Table I will be functional.

A suitable 5' promoter region for alpha-S1-casein can be isolated by PCR amplification from the *Bos taurus* alpha-S1-casein gene using the primers of SEQ ID Nos. 11–12 to yield a fragment comprising residues 8 through 3608 of the gene found in exon 2 of the genomic clone. The PCR primers of SEQ ID Nos. 11–12 also include an Aat II segment for use in cloning into the Aat II/Nhe I major site of the pGFP-C1 plasmid. A 3' promoter segment from *Bos taurus* alpha-S1-casein comprises residues 18438 (in exon 18) through 21576, and can be obtained with the PCR primers of SEQ ID Nos. 13–14. The alpha-S1-casein gene portions begins with residue 11 of each of the primers of SEQ ID Nos. 11–14.

TABLE I

MILK-SPECIFIC PROMOTERS

| | Species | Accession | Description |
|---|---|---|---|
| A. beta-lactoglobulin | *Bos taurus* (cow) | #X11996 | 5' region |
| | *Bos taurus* (cow) | #X14710 | |
| | *capra hircus* (goat) | #Z33881 | |
| | *Ovis aries* (sheep) | #X12817 | |
| | *Ovis sp.* (sheep) | #M32232 to M32237 | |
| | *Macropus eugenii* (marsupial) | #L14954 to L14960 | |
| B. alpha-s1-casein | *Bos taurus* | #X59856 | |

TABLE I-continued

MILK-SPECIFIC PROMOTERS

| | Species | Accession | Description |
|---|---|---|---|
| | *Bos taurus* | #X03590 | 5' flanking region |
| | *Oryctolagus cuniculus* (rabbit) | #M77195 | |
| | Bos species | #S57536 and S57539 | |
| C. alpha-s2-casein | *Bos taurus* | #M94327 | |
| D. beta-casein | *Bos taurus* | #M21342 to M21343 | |
| | *Bos taurus* | #M31707 | 5' region |
| | *Bos taurus* | #M55158 | |
| | *Bos taurus* | #X14711 | |
| | *Capra hircus* | #M90559 to M90562 | |
| | *Oryctolagus cuniculus* (rabbit) | #X15735 | |
| | *Oryctolagus cuniculus* (rabbit) | #M33582 | |
| E. kappa-casein | *Capra hircus* (goat) | #Z33882 | |
| | *Bos taurus* | #X14906 to X14908, X14326 | |
| | *Ovis aries* | #L31372 | |
| | *Bos taurus* (strain Holstein-Friesian) | #M75887 | |
| F. alpha-lactalbumin | *Bos taurus* | #M90645 | 5' UTR and 5' end of cds |
| | *Bos taurus* | #X06366 | |
| | *Capra hircus* (goat) | #M63868 | |
| A. beta-lactoglobulin | *Bos taurus* (cow) | #X14710 | |
| | *Capra hircus* (goat) | #Z33881 | |
| | *Ovis aries* (sheep) | #X12817 | |
| | *Ovis sp.* (sheep) | #M32232–M32237 | |
| | *Macropus eugenii* (marsupial) | #L14954 to L14960 | |
| B. alpha-s1-casein | *Bos taurus* | #X59856 | |
| | *Capra hircus* (goat) | #X56462 | |
| | *Oryctolagus cuniculus* (rabbit) | #M77195 | |
| C. alpha-s2-casein | *Bos taurus* | #M94327 | |
| D. beta-casein | *Bos taurus* | #M21342 to M21343 | |
| | *Bos taurus* | *#M31708 | |
| | *Bos taurus* | #M55158 | |
| | *Bos taurus* | #X14711 | |
| | *Capra hircus* | #M90559 to M90562 | |
| | *Oryctolagus cuniculus* (rabbit) | #M33582 | |
| E. kappa-casein | *Bos taurus* | #X14906 to X14908, X14326 | |
| | *Bos taurus* (strain Holstein-Friesian) | #M75888 | |
| F. alpha-lactalbumin | *Bos taurus* | #X06366 | |

The 5 segment primers include an Aat II restriction site linker adjacent residue 8 of the gene, and an Nhe I restriction site linker adjacent residue 3608 of the gene. The 3' segment primers include a Sal I restriction site linker adjacent residue 18438 of the gene, and an Apa I restriction site linker adjacent residue 21576. These restriction sites are useful for cloning into the multiple cloning site of pGFP-C1; however, different restriction sites could be produced as desired for cloning into a different plasmid.

Another set of 5' and 3' promoter segments which could be substituted for the beta casein promoter segments can be obtained by PCR amplification with the primer pairs of SEQ ID Nos. 15–16 and SEQ ID Nos. 17–18 from the goat (*Capra hircus*) beta-lactoglobulin genomic clone. The primers of SEQ ID Nos. 15–16 amplify the segment from residue 1 through residue 3050 (exon 2); primers of SEQ ID Nos. 17–18 amplify a 3' segment from residue 5946 through residue 7535. Here also, the beta lactoglobulin coding portion begins with residue 11 of each primer. The 5' segment primers include an Nhe I restriction site linker adjacent residue 1 of the gene, and an Age I restriction site linker adjacent residue 3050. The 3' segment primers include a Sal I restriction site linker adjacent residue 5946 of the gene, and a Bam HI restriction site linker adjacent residue 7535. As for the embodiment using alpha-S1-casein regulatory sequences, these restriction sites are selected to facilitate cloning into the multiple cloning site of pGFP-C1.

Desirably, the 5' segment of the milk-specific promoter should include a signal peptide encoding sequence which encodes a peptide that facilitates secretion of the transgene product. In the beta casein 5' region utilized in the construct of SEQ ID No. 5, the signal sequence is found in exon 2 and has an amino acid sequence Met-Lys-Val-Leu-Ile-Leu-Ala-Cys-Leu-Ala-Leu-Ala. The mature signal protein has an Arg residue immediately prior to the Met residue, this Arg residue being found in the signal sequence encoding regions of casein genes from cow, sheep, goat, pig, rat, mouse, rabbit, human, and kangaroo. More information concerning milk protein genes is available in "Structure and function of milk protein genes", J.-C. Mercier and J-L. Vilotte, *J. Dairy Science* 76:3079–3098 (1993).

The illustrated embodiments (SEQ ID Nos. 5 and 6) have Shiva-1 as the amphipathic peptide. However, other amphipathic peptide encoding genes can be substituted for Shiva-1. Presently preferred amphipathic peptides include Hecate-1, Hecate-2, Hecate-3, Shiva-1, Shiva-2, Shiva-6, Shiva-7, Shiva-9, SB-37, AP-7, Flak-1, and Manitou-1 (SEQ ID Nos. 19–30, respectively), along with cecropin-B, Anubis-1, -2, -3 and -4, Shiva-3, -4, -5, -8, and -10, melittin, and Vishnu series amphipathic peptides. It is understood that the cassette can further include a plurality of amphipathic peptide encoding genes adjacently linked in reading frame to each other.

Figure 5:
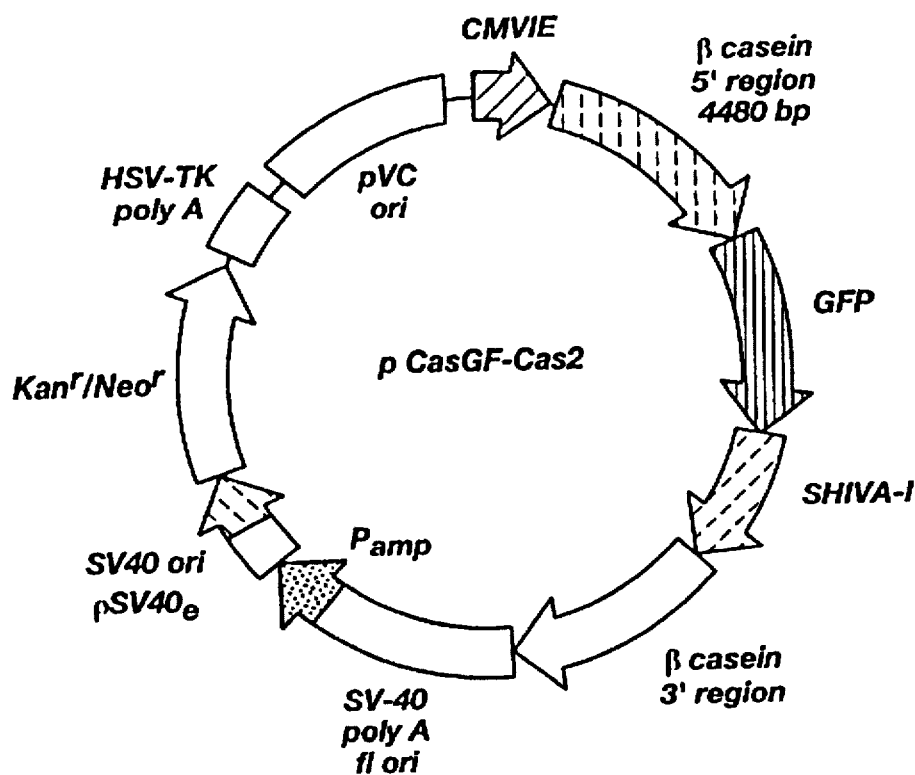
FIG. 5 depicts a map of an embodiment of a plasmid carrying the cassette of the invention, plasmid pCasGF-Cas2, derived from the plasmid pGFP-C1 shown in FIG. 4.
Figure 6:
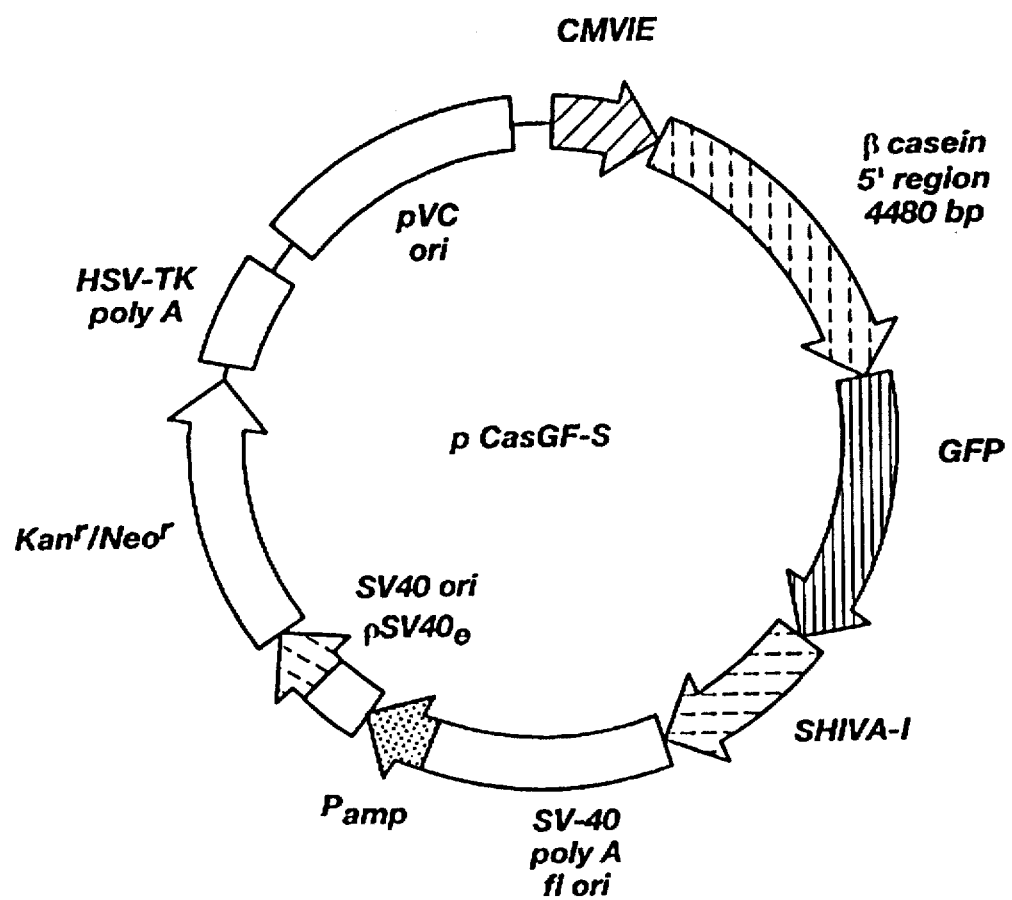
FIG. 6 depicts a map of a plasmid pCasGF-S carrying an alternate embodiment of a cassette of the invention.

In the presently preferred illustrated embodiments of SEQ ID Nos. 5 and 6, the cassette further includes a fusion peptide encoding gene, here embodied as GFP (green fluorescent protein) encoding gene, inserted in reading frame adjacent the amphipathic peptide encoding gene (FIGS. 5 and 6). One purpose of the fusion peptide gene is to inhibit toxic activity of the amphipathic peptide, which depends in large part on its amphipathic character. The fusion peptide encoding gene may be placed on either side of the amphipathic peptide encoding gene, but the placement should ensure that the chemical cleavage of the fusion peptide does not materially alter the amphipathic chemical character of the amphipathic peptide. An additional or alternate purpose served by an appropriately-chosen fusion peptide gene is to provide a marker or tag for detecting expression of the cassette and/or for facilitating isolation of the amphipathic peptide from milk.

In the embodiments illustrated in FIGS. 5 and 6 and in SEQ ID Nos. 5 and 6, the fusion peptide is GFP, otherwise known as "green fluorescent protein". The GFP can be detected by fluorescence at between about 509 nm and 540 nm, with stimulation at between about 340 nm and about 490 nm. In the illustrated embodiments, the GFP coding sequence is placed adjacently upstream of the amphipathic peptide coding sequence, so that the cyanogen bromide cleavage of the amphipathic peptide from the GFP will not significantly alter the amphipathicity of the peptide. A protocol for cleavage of amphipathic peptide from the fusion product using cyanogen bromide is described in the literature in, for example, "Chemical cleavage of fusion proteins using cyanogen bromide", E. R. LaValli and J. M. McCoy, p. 16.4.11–16.4.12 in *Current Protocols in Molecular Biology* (F. M. Ausubel et al., eds; John Wiley and Sons, Inc., New York, pub.; 1994).

A cassette expressing a GFP-Shiva 1 fusion product under the control of the CMV promoter from the pGFP-C1 plasmid has been stably integrated into mink embryonic stem cells. Expression of the fusion peptide was observed as GFP fluorescence; GFP-Shiva-1 stable transfectants exhibited a fluorescence approximately three-fold higher than negative controls. This expression of the fusion product in the transfectant cells did not produce any significant effects on cell growth rate or cell death. This result indicates that Shiva-1 can be expressed in mammalian cells as a fusion product without deleterious effects on the cells.

Many other fusion peptides could be substituted for GFP. One such fusion peptide is the so-called streptavidin tag, a nine amino acid peptide that binds streptavidin and thus is useful to purify the expressed fusion product (the amphipathic peptide with the fusion peptide attached at one terminus) by streptavidin affinity (see "One-step affinity purification of bacterially produced proteins by means of the strep tag and immobilized recombinant core streptavidin", T. G. Schmidt and A. Skerra, *J. Chromatography A.* 676:337–345, 1994). Another group of proteins useful as the fusion peptide are milk proteins themselves, such as beta casein, alpha-S1-casein, alpha-S2-casein, beta-lactoglobulin, kappa-casein, alpha-lactalbumin, and the like. A particularly preferred embodiment would use a milk protein such as kappa-casein which is incorporated into the micelles of milk, which are easily separated from the bulk milk. Alternatively, the fusion peptide can be embodied as a histidine segment comprising at least six consecutive histidine residues, which can be used to purify the expressed fusion product via a resin containing nickel ions. In still another embodiment, the histidine segment is added to the terminus of a different fusion peptide, the latter being adjacent the amphipathic peptide, primarily to facilitate purification. Still other useful fusion peptides are beta galactosidase and trpE, either of which can be readily purified by antibody affinity chromatography to pull out the fusion product. A further advantage of beta galactosidase is that its presence can be monitored during purification. In all cases, the fusion peptide gene must be inserted in reading frame with the amphipathic peptide. Also, the linkage of the fusion peptide to the amphipathic peptide must be such that it can be readily cleaved from the amphipathic peptide without significantly altering the properties of the amphipathic peptide.

Depending on which fusion peptide is selected for the cassette, alternative cleavage methods other than cyanogen bromide could be used, including proteolytic cleavage. In such case, the junction of the fusion peptide coding sequence with the amphipathic peptide coding sequence is engineered to produce a site for proteolytic cleavage which will result in liberation of a functional amphipathic peptide. Presently preferred proteolytic enzymes are ones known to clot or be active in milk, most or all of which are already FDA-approved as safe. These preferred proteolytic enzymes include: porcine, bovine, and chicken pepsins; rennet enzymes from fungus, including *Endothia parasitica* rennet, *Mucor pusillus* var. *Lindt* rennet, and *Mucor miehei* rennet; and *Bacillus cereus* protease. Enzymes such as papain, chymopapain, ficin and bromelain could also be used, but these may not be FDA-approved and therefore are presently considered less desirable.

While the illustrated embodiments include a fusion peptide encoding gene, it is believed that for at least some amphipathic peptides a fusion peptide is not required to prevent toxicity to the milk producing cells. Since the expression of the amphipathic peptide occurs only in milk-producing cells and when milk production is stimulated by a secretory-signal-containing regulatory region, the amphipathic peptide may become associated with the lipids in vesicles which in turn join micelles in the milk. The amphipathic peptide may thus in effect be sequestered, such that the effective intracellular and/or extracellular concentrations are below toxic levels. Thus, still another embodiment of the cassette comprises a milk-specific protein 5' regulatory region adjacently linked to the 5' end of, and in reading frame with, an amphipathic peptide-encoding gene. The cassette further includes a 3' regulatory region providing for post-translational processing, which may also be derived from a milk-specific protein gene or may come from another source such as SV-40.

In an embodiment for insertion into mammalian cells in culture, the cassette should further include at least one selection marker to facilitate selection of mammalian cells which have incorporated the cassette into their genomic DNA. The mammalian selection marker may however be omitted from a cassette intended for microinjection into embryos. The cassette also desirably includes a bacterial selection marker to facilitate production of the cassette in bacteria, as known in the art. In the embodiments of SEQ ID Nos. 5 and 6, the cassette further includes the portion of the pGFP-C1 plasmid which encodes both kanamycin and neomycin resistance genes under the control of a promoter segment which provides for expression in either bacterial or mammalian cells.

The embodiments of SEQ ID Nos. 5 and 6 and FIGS. 5 and 6 are constructed from the commercially available pGFP-C1 plasmid, whose multiple cloning site ("MCS") is designed such that insertion of a gene downstream from the GFP coding sequence will be aligned in the reading frame with GFP. The pGFP-C1 plasmid also provides many desirable auxiliary items, including a 3' regulatory region with an SV-40 polyadenylation signal and selection markers for both bacterial and mammalian cells under appropriate regulatory controls.

In the embodiment of SEQ ID No. 5, pGFP-C1 is modified such that the segment beyond residue 126 of pGFP-C1 through the start of the 3' SV-40 region is that of SEQ ID No. 5 to produce a plasmid herein designated pCasGF-SCas. This modification disrupts the CMV promoter segment. A second illustrated embodiment referred to as plasmid pCasGF-S, comprises the pGFP-C1 plasmid modified to contain SEQ ID No. 6 instead of SEQ ID No. 5. To accomplish these substitutions, a segment comprising residues 127–4586 of SEQ ID Nos. 5 or 6 (this region is the same in both SEQ ID Nos. 5 and 6) is inserted in pGFP-C1 upstream and in reading frame with the GFP coding sequence. The insertion is accomplished by means of Aat II/Nhe I restriction sites, and with concomitant deletion of the remainder of the CMV promoter beyond residue 126 of pGFP-C1. The Shiva-1 coding sequence comprising residues 5330–5448 of SEQ ID No. 5 is inserted downstream of the GFP coding sequence in the pGFP-C1 multiple cloning site. In pCasGF-Cas2, this insertion further includes a segment comprising residues 5449–7760 of SEQ ID No. 5 which comprise the beta casein 3' regulatory region. The segments comprising the 5' and 3' beta casein regulatory regions are obtained from the with the appropriate primer pairs SEQ ID Nos. 7–8 and 9–10 as described previously herein, the primer pairs being constructed to introduce the necessary restriction sites.

Desirably, as is known in the art, the cassette should include at least one selection marker to facilitate selection of mammalian cells which have incorporated the cassette into their genomic DNA. In the embodiments of SEQ ID Nos. 5 and 6, the cassette includes the portion of the pGFP-C1 plasmid which encodes both kanamycin and neomycin resistance genes under the control of a promoter segment which provides for expression in either bacterial or mammalian cells.

Insertion of the cassette into a mammalian organism, and screening of resulting organisms, may be accomplished by micro-injection into embryos according to the general protocols described subsequently herein in Examples 2 and 3. The cassette may alternatively be inserted into cultured cells, including stem cells to be introduced into a host organism, by transfection of a linearized construct or linearized plasmid carrying the construct, or of supercoiled plasmid carrying the construct. Lipofection of supercoiled plasmid is the presently preferred method of transfection.

In a further preferred embodiment, the transgenic organism is prepared by co-transfection of two or more cassettes each containing a milk-specific promoter controlling an amphipathic peptide gene. The milk-specific promoter may desirably differ for each cassette. The amphipathic peptide gene may be the same for all cassettes or may differ as well. Co-integration of two or more cassettes is believed to produce a synergistic, i.e. greater than additive, enhancement of expression of the fusion product.

Figure 7:
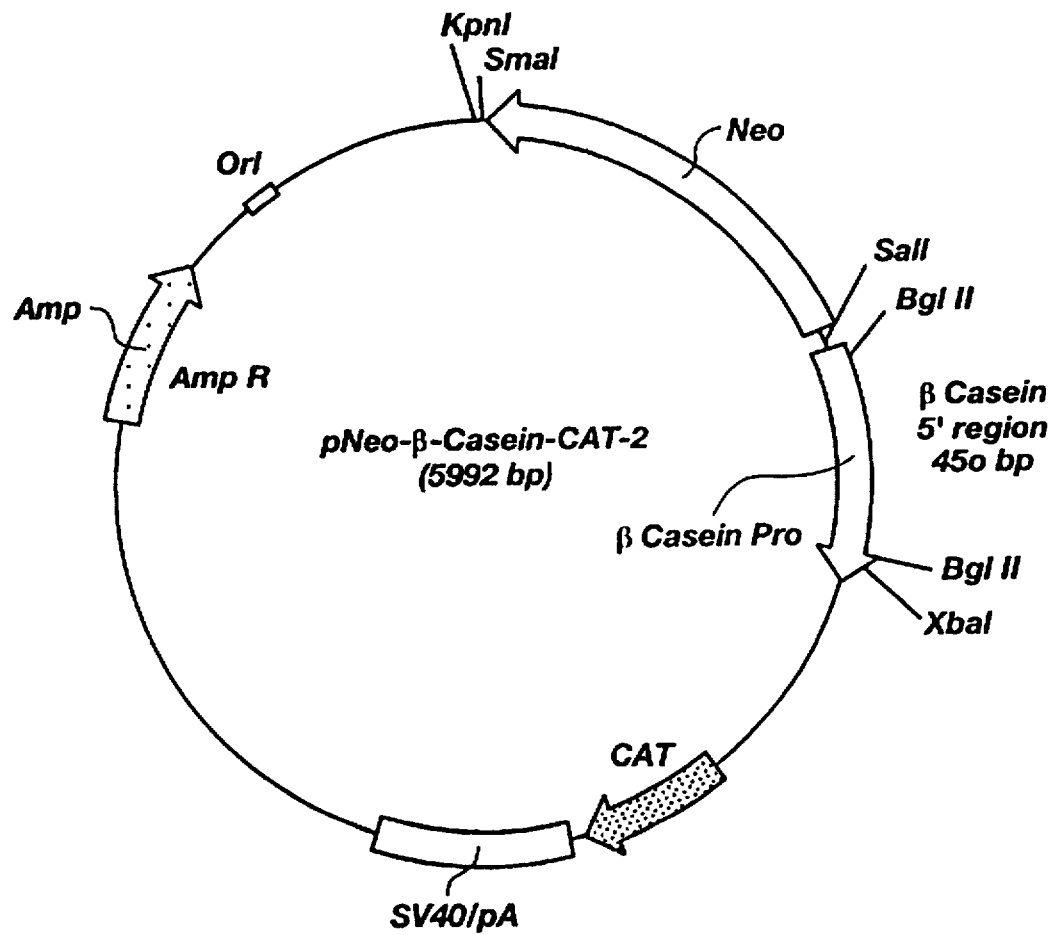
FIG. 7 depicts a map of a plasmid pNeo-beta-casCAT2, which contains a chloramphenicol acetyl transferase gene under the regulatory control of a beta-casein 5' promoter region, used in EXAMPLE 1.

FIG. 7 depicts a plasmid pNeo-beta-casCAT2 having a cassette comprising a beta casein 5' regulatory sequence upstream of the CAT gene expressing chloramphenicol acetyl transferase enzyme. The beta casein 5' sequence comprises a 450 base pair segment extending from −310 to +140 of the genomic clone of the *Bos taurus* beta casein gene (GENBANK accession # M14711), and in this plasmid has been inserted in multiple cloning site MCS I of plasmid pHE ($P_r$-$E_n$-)CAT (available from 5 Prime→3 Prime, Inc., Boulder, Colo.; lacks a promoter for the CAT gene). In this location, the beta casein 5' sequence regulates the CAT gene from of plasmid pHE ($P_r$-$E_n$-)CAT. The beta casein gene segment was obtained using the primers of SEQ. ID Nos. 31–32 to amplify a 1559-bp portion of the beta casein genomic clone GENBANK accession # M14711, and cleaving with BGIII to yield a 450 base-pair segment. The final 450 bp beta casein segment inserted into the cassette comprises the 5' flanking sequences including CAAT box, TATA box, progesterone-regulatory region, glucocorticoid regulatory region, CTF/NF-1 nuclear protein binding sites, and mammary gland specific factor binding site (Gorodetsky et al. op cit; see also S. Altiok and B. Groner, "Interaction of two sequence specific single-stranded DNA-binding proteins with an essential region of the beta casein gene promoter is regulated by lactogenic hormones", *Mol.Cell-.Biol.* 13:7303–7310, 1993; J. Nowock, V. Borgmeyer, A. W. Puschel, R. A. W. Rupp, and A. E. Seppel, "The TGGCA-binding protein binds to the MMTV-LTR, the adenovirus origin of replication, and the BK virus enhancer", *Nucleic Acids Res.* 13:2045–2061). The 450-bp segment also includes the transcription start site, the first exon, and a 5' portion of the first intron. This 450-bp segment appears to comprise the minimum portion of the beta casein gene needed for hormone-responsive transcription of beta casein gene. However, it is believed that other 5' and 3' portions of the gene may further enhance beta casein transcription and/or translation or provide responsiveness to additional lactogenic hormones or enhancers.

Additionally, the cassette includes a segment comprising SV-40 polyadenylation signal and splice site inserted adjacent and downstream of the CAT gene to provide for post-translational processing. The plasmid used in the expression studies further included a mammalian selection marker cassette, which comprised the neo gene driven by the mouse thymidine kinase promoter and polyoma virus enhancer PyF441 derived from plasmid pMC1 NeoPolyA (available from Stratagene, Calif.), and a bacterial selection marker. The plasmid used in the expression studies was designated pNeo-beta-casCAT2, and contained the neo and beta casein cassettes transcribing in opposite directions.

EXAMPLE 1

The cassette of FIG. 7, pNeo-beta-casCAT2, was transfected into HC11 cells and stable transformants were selected. The HC11 cell line has the ability to maintain in vitro production of beta casein under the regulation of the native beta casein 5' regulatory regions when appropriately treated with lactogenic hormones (W. Doppler, B. Groner and R. K. Ball, "Prolactin and glucocorticoid hormones synergistically induce expression of transfected rat beta-casein gene promoter constructs in a mammary epithelial cell line", PNAS 86:104–108, 1989; S. L. Gorodetsky, T. M. Tkach and T. B. Kapelinskaya, "Isolation and characterization of the Bos taurus beta casein gene", Gene 66:87–96, 1988). Additionally, groups of HC11 cells were transfected with one of the following: pHE ($P_r$–$E_n$–)CAT, as a negative transcription control; or pHE ($P_r$–$E_n$+)CAT (also available from 5 Prime→3 Prime, Inc.; includes an SV-40 promoter for CAT gene) as a positive transcription control.

The stable transfectant cell cultures were grown approximately to confluency and treated with different combinations of the lactogenic hormones dexamethasone ($10_{-7}$ molar), prolactin (5 µg/ml), and insulin (5 µg/ml) to induce beta casein transcription. CAT expression was measured approximately three days following the start of treatment. CAT gene expression was measured as CAT enzyme activity, and CAT protein levels were assayed using an indirect immunofluorescence kit obtained from 5 Prime→3 Prime, Inc., according to the manufacturer's instructions. Tables II and III contain data showing the results of these studies.

TABLE II

Effect of lactogenic hormones on expression of pNeo β casCAT2 transfected into HC11

| Hormone added | | | CAT activity, nmole per min per mg of protein | Introduction ratio fold |
|---|---|---|---|---|
| Pro | Dex | Ins | | |
| − | − | − | 0.29 ± 0.13* | 1 |
| + | + | + | 2.26 ± 0.56* | 7.8 |

Stably transfected HC11 cells were kept at full confluence level in growth medium for 3 days and then incubated with hormones for 3 days.
The hormone concentrations were as follows:
prolactin (Pri), 5 µg/ml;
dexamethasone (Dex), 0.1 µM;
insulin (Ins), 5 µg/ml

TABLE II-continued

Effect of lactogenic hormones on expression of pNeo β casCAT2 transfected into HC11

| Hormone added | | | CAT activity, nmole per min per mg of protein | Introduction ratio fold |
|---|---|---|---|---|
| Pro | Dex | Ins | | |

*Means ± SEM of five experiments three pools of cells derived from individual transfections.

TABLE III

Effect of lactogenic hormones on expression of pNEO-β-casCAT2 transfected into HC11

| Hormone added | | | CAT activity, nmole per min per mg of protein | Introduction ratio fold |
|---|---|---|---|---|
| Pro | Dex | Ins | | |
| − | − | − | 0.4 | 1 |
| + | + | − | 0.9 | 2.3 |
| − | − | − | 0.55 | 1.4 |
| + | − | − | 0.8 | 2 |
| − | − | + | 0.4 | 1 |

Stably transfected HC11 cells were kept at confluence for 3 days and then incubated with hormones for 3 days. The hormone concentrations were as shown for table 1.
No duplicates were performed, therefore Mean ± SEM was not calculated for the given data.

In the absence of the hormone treatments, CAT expression was at a basal level. Either dexamethasone alone or prolactin alone induced CAT expression at levels greater than basal. A mixture of prolactin and dexamethasone produced a 2.3 fold induction, while the strongest response was a 7-fold induction produced by a combination of prolactin, dexamethasone and insulin all added simultaneously. Significant CAT expression was also observed in the cells incorporating the SV-40-promoter-CAT construct from pHE ($P_r$+$E_n$+)CAT. In comparison, no induction of CAT activity was observed in cells incorporating the promoterless-CAT construct (pHE ($P_r$–$E_n$–)CAT.

In an alternate embodiment of a cassette for expression of amphipathic peptides in mammalian organisms, the regulatory sequence used is that normally associated with regulation of the interleukin-2 gene. This embodiment is useful to produce disease-resistant animals and in treatment of certain diseases by incorporation into stem cells which are to be re-introduced into the diseased host. Interleukin-2 (IL-2) is a growth factor for thymus-derived lymphocytes (commonly referred to as "T cells"), and is only synthesized by "activated" T cells. Activation occurs as a result of interaction between a T cell and the surface of a macrophage which has itself interacted with an antigen or pathogen-infected cell; it is believed that the macrophage presents an antigen to the T cell as part of this process. Activation of the T cell in turn triggers synthesis of IL-2. The IL-2 noncoding sequences (control or regulatory sequences) adjacent the IL-2 coding sequences have been determined to be required for this triggering of IL-2 synthesis upon activation of the T cell.

The regulatory region of the IL-2 gene includes a noncoding promoter sequence and a signal sequence downstream of the promoter. This signal sequence is transcribed to form a signal peptide preceding the IL-2 gene product, which helps target the gene product for secretion by a mammalian cell. The signal peptide is cleaved from the gene product within the cell and prior to secretion. To obtain the desired antimicrobial effects of the expressed amphipathic peptide, it is highly preferred that the amphipathic peptide be secreted.

Since activation of a T cell is associated with activity of the immune system in response to an actual or potential disease state, the IL-2 regulating sequences are ideal for controlling the expression of an amphipathic peptide. Further, as mentioned previously, IL-2 is produced only in T cells. Thus, in making a transgenic animal carrying a gene for an amphipathic peptide under the IL-2 regulatory control, one avoids the problem of having the amphipathic peptide synthesized in all tissues and potentially causing harm to the animal. In the present invention, the amphipathic peptide is effectively delivered primarily at the appropriate site, e.g. adjacent the pathogenic organism or in the lymphoid system where it may contact the pathogen. Also, the amphipathic peptide is synthesized in significant amounts only when required by the existence of a disease state which triggers activation of T cells.

A further desirable feature for regulating sequences to control expression of an amphipathic peptide is that they provide "tight" control of expression. By "tight" expression, it is meant that there is essentially no detectable gene product produced in the absence of the "trigger" signal. The IL-2 regulating sequences appear to regulate expression more tightly than do the regulating sequences associated with most other interleukins, with the exception of interleukin-12. Thus, the tight expression provided by the IL-2 promoter is a further advantage of the cassette for the production of transgenic organisms.

U.S. Pat. No. 4,992,367 to Cullen discusses methods and compositions for enhancing the expression of interleukin-2 in mammalian cells, involving substitution of the rat IL-2 control sequences for the "native" human IL-2 control sequences. U.S. Pat. No. 4,952,499 to Cantor et al. discloses certain other genes and gene products which regulate expression of the IL-2 receptor. This receptor is found on the surfaces of T cells, and binding of IL-2 to this highly specific receptor is part of the mechanism by which IL-2 stimulates reproduction of activated T cells.

In the instant embodiment, in which production of transgenic mice was used to demonstrate the feasibility of the invention, the interleukin-2 promoter was obtained from mouse genomic DNA using a polymerase chain reaction (PCR). A crude extract of DNA was made from Swiss Albino mouse 3T3 fibroblast cells (ATCC #CCL 92), and primers as shown in SEQ. ID#1 and #2 were used for the PCR reaction to amplify a portion of the mouse IL-2 gene from nucleotides −593 to +110. In the numbering scheme to which the aforementioned nucleotide numbers refer, "1" is taken to be the first nucleotide of the segment coding for the IL-2 protein. In the natural host organism, it is known that binding sites for NF-kappa-B, NF-AT, AP-1, AP-3 and Oct-1 are found in the region from nucleotides −593 to −1 of the complete IL-2 gene. The complete sequence of this region is on record with EMBL with accession No. X52618. In addition, in vivo in the mouse genome there is a segment between the regulatory sequences and the IL-2 coding sequence, which is a so-called "signal" sequence. This segment (from nucleotides +1 to +110 in the IL-2 gene) is transcribed and translated but is cleaved from the IL-2 protein after its passage into the endoplasmic reticulum. The signal sequence segment has been published by Fuse et al., *Nucleic Acids Res.* 12:9323 (1984).

The upstream primer (SEQ. ID #1) has a sequence complementary to the anti-sense strand (e.g., to bind to the antisense strand), while the downstream primer SEQ. ID #2) has a sequence complementary to the sense strand. Additionally, in this embodiment there are six additional nucleotides on the upstream end of the upstream primer (SEQ. ID #1) and seven additional nucleotides on the downstream end of the downstream end which are not part of the native sequence, and which were added in order to form, respectively, SalI and BglII restriction enzyme recognition sites. These restriction sites were added to aid in cloning and placement next to the amphipathic peptide coding sequence to form the cassette, and for preparing the cassette for transfer into embryos. These two restriction sites were selected for convenience; others could be used if desired. The primers were of sufficient length (twenty-five nucleotides) that the short non-homologous regions at the ends did not interfere with adequate amplification of the desired IL-2-regulon sequences.

The PCR-reacted DNA was run on a gel, and a band of about 715 nucleotides in length corresponding to the expected length of the amplified fragment was isolated and identified. The amplified fragment contains the major up-regulatory, cis-acting control sequences of the 5' flanking region of the IL-2 gene, a TATA box, a PstI site at +43, the sequence encoding the 21 amino acid signal peptide, and the added SalI and BglII restriction sites. The amplified fragment was isolated from this band, made blunt-ended, and cloned into the SmaI site of pUC18 (commercially available from several suppliers, including U.S. Biochemical, Cleveland Ohio, cat. # 70070; BRL Life Technologies, Gaithersburg Md., cat. #5363SA; and Boehringer Mannheim Corp., Indianapolis Ind., cat. #885797). The resulting plasmid was termed pUC-IL.

Shiva-1 is a 38-amino acid polypeptide having seq. ID #3. The sequence for Shiva-1 and for other amphipathic peptides and amphipathic peptide homologues can be found in PCT (World) patent publication no. WO 89/00194. In the present case, the Shiva-1 coding sequence was removed from plasmid pMON530 (obtained from Jaynes et al) by digestion with BglII and EcoRI. The Shiva-1 fragment was separated by electrophoresis and purified from the gel. Plasmid pUC-IL was digested with BglII and EcoRI, and the Shiva-1 coding fragment was ligated into the gap, such that it was in frame with the signal sequence. The plasmid was tested by restriction digest analysis and by sequencing to determine that it carried the correct insert. The sequence of the complete insert is submitted as SEQ. ID #3 with this application. The plasmid containing the insert having SEQ. ID #3 is referred to as "pILSHI". Subsequently, an SV-40 sequence encoding polyadenylation and mRNA splicing signals was added to the 3' end of the Shiva-1 coding segment to provide for completion of this phase of post-translational processing. This plasmid is referred to as pILSHI-X.

Also, a NEO expression cassette (a selectable marker conferring neomycin resistance) was taken from plasmid pMC1 NeoPolA (FIG. 1; available from Stratagene, La Jolla Calif. 92037, catalog no. 213201) by cutting the plasmid with Xho I and Sal I. The fragment corresponding to the NEO cassette was then purified and subcloned into the pILSHI and pILSHI-X plasmids at the SalI site upstream of the IL-2/Shiva-1 sequences, and in reverse orientation to those sequences. The resulting plasmids are respectively referred to as "pILSHI/neo" and "pILSHI-X/neo". These plasmids both contain the IL-2 promoter and signal sequences adjacent the Shiva-1 coding sequence, a fusion peptide sequence coding for three amino acids (Arg, Ser, Thr) which intervenes between the signal sequence and the Shiva-1 coding sequence, and the NEO gene under the control of the thymidine kinase promoter. Plasmid pILSHI-X/neo further includes the SV-40 polyadenylation and splice signals, downstream of the Shiva-1 coding sequence.

The NEO marker is optional, as it is not needed for the production of transgenic animals (multicellular organisms), but it is highly desirable for transfections into unicellular organisms such as in vitro cultured cells. Other suitable selectable markers could be used in place of NEO for the cassette.

The pILSHI/neo, pILSHI-X or pILSHI-X/neo plasmids can be propagated in appropriate bacterial strains. Presently, they are being propagated in *E. coli* strain DH5αMCR (available from BRL, Gaithersburg, Md.), which is methylase-defective.

Figure 3:
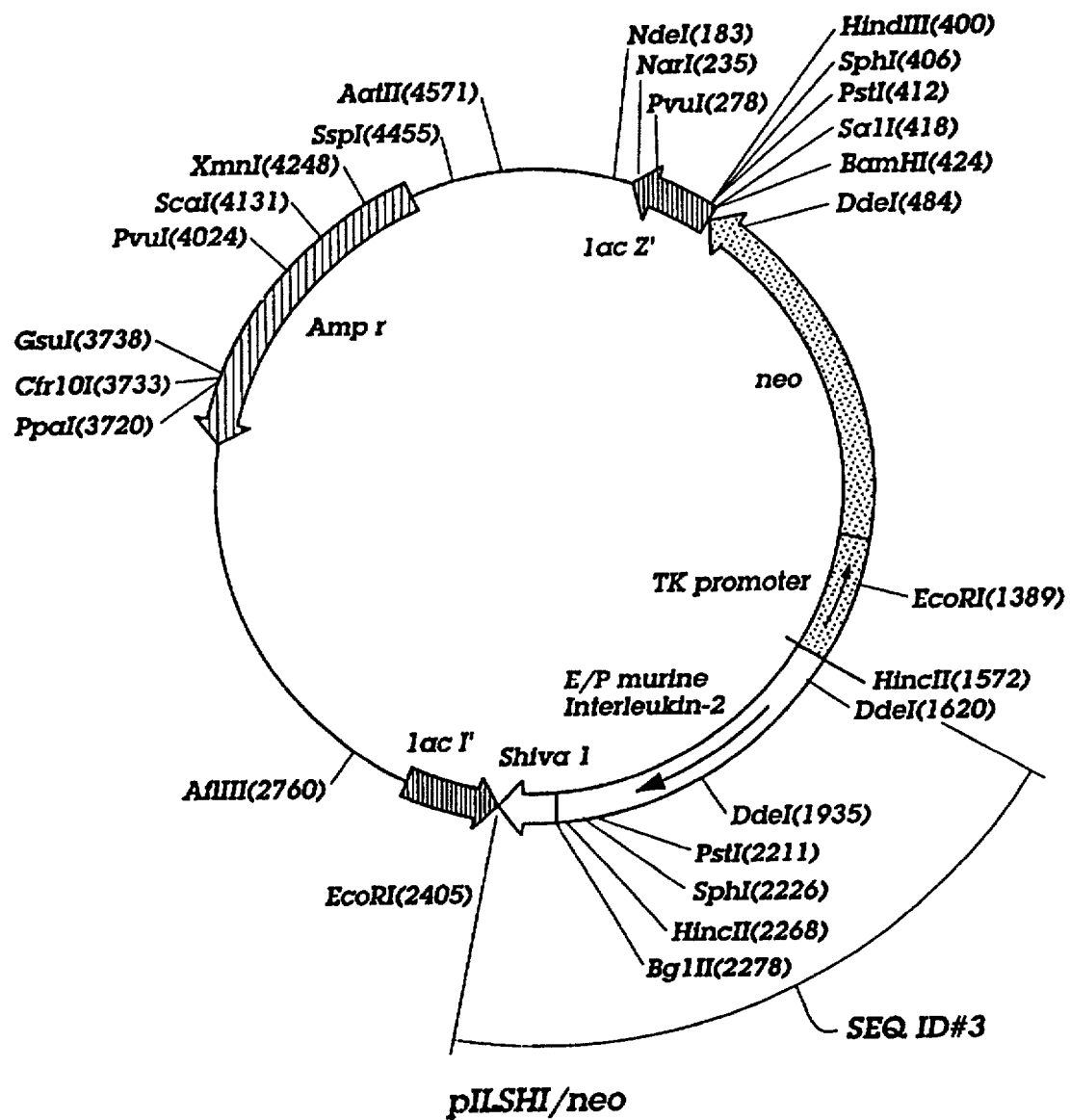
FIG. 3 depicts a map of a plasmid designated pILSHI/neo which carries an embodiment of the DNA cassette of the invention.
Figure 4:
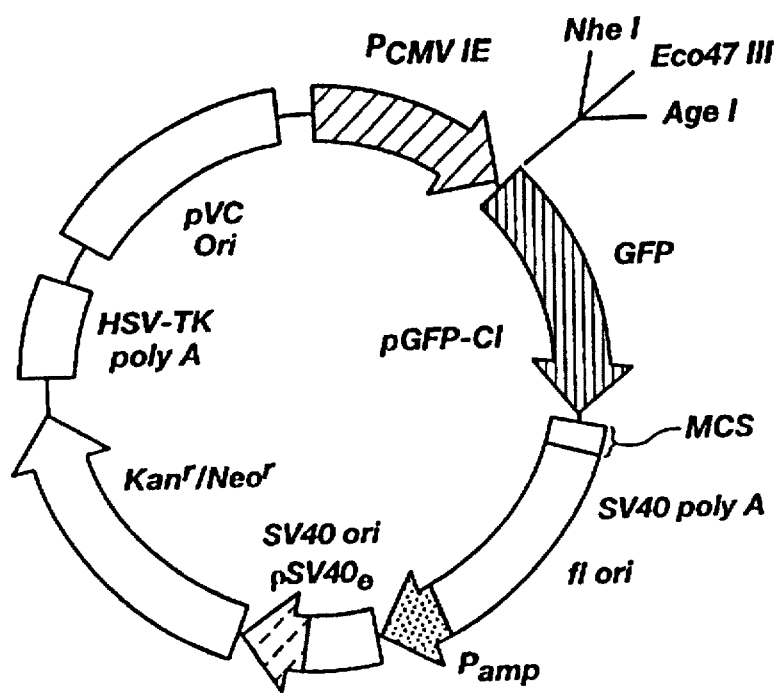
FIG. 4 depicts a map of a commercially available plasmid pGFP-C1 carrying a GFP peptide-encoding segment.

A cassette according to the invention may be introduced into a living host by any appropriate method. It is presently preferred to prepare the cassette DNA to a size of less than about 15 kilobases for insertion. In the embodiment of FIG. 3, this can be done by digestion with PvuI, which cuts at the indicated sites to produce a fragment which is 5422 basepairs in length. Preferably also, the fragment which carries the cassette is separated from the remaining DNA before insertion.

Insertion of the cassette into the genomes of tissue culture cells or cells and tissues removed from a host, can be performed as known in the art by electroporation, microinjection, and the like. For this purpose, the cassette desirably contains a marker permitting selection of cells which have integrated the cassette, such as the neomycin resistance gene commonly known as NEO.

Insertion of the cassette into the genome of a multicellular organism may be accomplished by injection into early embryos. For this purpose, the cassette need not contain a selection marker. It is highly desirable that the cassette be integrated into the genome of the germ cells, so that the cassette will be transmitted to subsequent generations stemming from the original engineered organism. It will generally be necessary to screen the animals which result from the injected embryos to ascertain which have the cassette in their DNA. It may further be desirable to screen either selected tissues or the first generation offspring of the engineered animals, to determine whether the cassette is present in the germline cells.

In an alternate embodiment, the regulatory segment may be the c-myc promoter. The c-myc gene is also selectively expressed in certain cells and in response to disease and wound-related conditions. For example, c-myc is expressed in activated T cells (like IL-2) and in fibroblasts at wound sites. Its expression is also stimulated by growth factors.

Amphipathic peptides (when present at low and non-toxic levels) also have the property of stimulating proliferation in mammalian and other cells. Thus, the selective expression of amphipathic peptides in a wound is expected to speed healing of the wound in addition to preventing infection in the area. The sequence for the c-myc gene has been determined and is available under accession #L00038 from EMBL.

In a further embodiment specifically directed at improved wound-healing or stimulation of cell growth, the cassette comprises the c-myc promoter linked to Vishnu-1 or an amphipathic peptide analogue having similar properties. Vishnu1 is a truncated version of Shiva1 which lacks the cytolytic and toxic properties of Shiva-1, but still induces proliferation of mammalian and bacterial cells.

EXAMPLE 2

Production of transgenic mouse carrying the cassette

Preparation of DNA for Injection into Embryos

A PvuI restriction enzyme digest of pILSHI/neo was performed to linearize the DNA and remove a portion of the vector not required for mammalian cell expression. The fragment was purified by agarose gel electrophoresis and separated from the gel slice using GeneClean (Bio 101, La Jolla, Calif., 92038–2284). The DNA was eluted from the glass beads using 10 μL of injection buffer (10 nM tris, 0.15 mM EDTA, pH 7.4). The solution was then dialyzed through a 0.025 μm pore size mixed esters of cellulose filter membrane (Millipore, Bedford, Mass., 91013) against three changes of a 10 mL pool of injection buffer over 72 h. The DNA concentration of the recovered solution was determined by staining with ethidium bromide and comparing against standards, then the concentration of the solution was adjusted to 2.5 ng/μL.

PREPARATION AND MICROINJECTION OF EMBRYOS AND TRANSFER INTO RECIPIENT FEMALES

Twenty-five six-week old female mice of strain B6SJLF1/J (Jackson Laboratory) were used as embryo donors. Twelve hours before the midpoint of the daily dark cycle, they were given intraperitoneal (IP) injections of seven IU (International Units) of pregnant mare serum gonadotropin (PMSG). Forty-seven hours later, the mice were given IP injections of 7 IU of human chorionic gonadotropin (hCG). Immediately after the hCG injections, they were transferred to cages containing proven fertile males of the same strain. No more than two females were in with each male. The donor females were left with the males for 22 hours, then removed and checked for a vaginal plug. Those with plugs were humanely killed, and the reproductive tract was removed and washed in M2 medium. Embryos were released from the ampullar region of the oviduct of these uteri into M2 medium. The embryos were washed in fresh medium, then transferred to M2 medium containing 1 mg/ml hyaluronidase and flushed gently within a small bore pipet to remove cumulus cells. They were then transferred to M2 medium without hyaluronidase, and placed in an incubator at 37° C., 5% $CO_2$ in air atmosphere, to await microinjection and transfer.

Forty-five six and eight week old CD1 (Jackson Laboratory) and FVB/N (Teconic Labs) female mice were used as the recipient females. The same hormone protocol described for preparation of the donor females, was used to prepare the recipient females. The prepared recipient females were induced to pseudopregnancy by mating with vasectomized males (strain C57/B).

As quickly as possible following removal from the donor females, an aliquot of the DNA solution (see above) was microinjected into the pronucleus of each embryo. The microinjected embryos were then transferred into the oviduct of congenic female mice. Microinjection into the pronucleus was performed basically as described by Allen et al. (in: *Mammalian Development*, a practical approach, M. Monk, editor, Irl Press, Oxford, England, 1987). On the average, the time the embryos were in M2 medium in the incubator, was generally around 40 min prior to microinjection and 15 to 60 minutes between micro-injection and transfer into recipient females, for a total of about 1–2 hours. Manipulations were carried out at room temperature in air.

Injected embryos were transferred using a glass pipette to the oviducts of recipient females anesthetized with tribromoethanol (Avertin), through bilateral flank incisions. Ten to fifteen embryos were transferred to each side. A total of ten recipients were used, of which three delivered live litters at normal gestational term. Nineteen pups survived to weaning at three weeks of age.

EXAMPLE 3

Screening for Transgenic Animals from Example 2

A PCR reaction using mouse tail DNA as template and primers which amplify both native interleukin-2 promoter and the IL2/Shiva 1/neo introduced fragment was performed as the primary detection technique.

At weaning, a 1.5 cm length of tissue was cut from the end of each pup∝s tail and digested overnight in Tail Extraction Buffer (100 mM tris, 5 nM EDTA, 0.20SDS, 200 mM NaCl, 0.1mg/mL proteinase K as described by R. Huntress, DNX Inc.). Hair and other undigested tissue was pelletted and the supernatant transferred to a fresh tube containing two volumes of ethanol. Precipitation was carried out over night at 20° C., the precipitate pelletted by centrifugation, and the dried pellet resuspended in 200 µL of TE buffer (10 mM tris, 1 nM EDTA, pH 7.6).

One microliter of the mouse tail DNA solution was added to the standard reaction described by Perkin Elmer Cetus (Norwalk, Conn., 06859) and 40 pMol of a primer for the interleukin-2 5'-flanking region, TAGATCTTGCGCTGT-TGACAAGGAG; 20 pMol of a primer for the interleukin-2 signal sequence, AGTCGACAACGACAAAATAGTACCT; and 20 pMol of a primer for the coding region of the NEO gene, CCACCATGATATTCGGCAAGC. This combination amplifies two regions of transgenic mouse genomic DNA but only one of native mouse DNA. To increase the sensitivity of the detection, a Southern blot was performed as directed in the instructions for the Polar Plex Chemileuminescent Blotting Kit (Millipore) using whole linearized pILSHI/neo plasmid labeled with biotin as a probe. Of the 19 mouse pups tested, one tested positive for the transgene.

EXAMPLE 4

Production of Additional Transgenic Mice Carrying the Cassette

A BamH1 digest of pILSHI-X/neo was prepared as in Example 1. Twenty-five six-week old female mice of strain FVB/N (Taconic Farms, Md.) were used as embryo donors; these were treated essentially as in Example 1 to produce embryos. The embryos were micro-injected also as described previously herein. Forty-five six- to eight-week old recipient female Swiss Webster mice (Taconic Farms) were induced to pseudopregnancy by mating with vasectomized Swiss Webster strain males. Micro-injected embryos were implanted into a total of 13 (thirteen) recipient females, of which 12 delivered live litters at the normal gestational term. Seventy-eight pups survived to weaning (three weeks), at which time samples of tissue were taken for screening as described in Example 2. Of the 78 mouse pups, 26 (twenty-six) tested positive for the transgene by PCR. Twelve transgenic lines carrying the transgene were subsequently established by breeding from these 26 individuals.

EXAMPLE 5

Spleen-derived lymphocytes were isolated from F2 generation offspring of six lines of transgenic mice from Example 4, and stimulated with concanavalin-A. Transcription of Shiva-1 was measured by reverse transcription of total mRNA from the lymphocytes and PCR amplification targeted to the Shiva-1 coding sequence. In the PCR amplification, Shiva-1 encoding mRNA was observed in lymphocyte samples derived from 3 different individuals from one line of transgenic mice. It was noted that mice from the line in which Shiva-1 transcription was observed did not exhibit any deleterious effects as to growth or general health.

The cassette of the invention is useful for numerous purposes. First, it may be used to produce transgenic animals which have resistance to disease, particularly to organisms which are susceptible to killing by amphipathic peptides. Such a disease-resistant trait would be useful in cows, sheep, pigs, chickens, and other domestic animals, as it would reduce the frequency and severity of common bacterial, fungal and protozoan infections. Since amphipathic peptides can also attack mammalian cells infected by some viruses, viral infections could also be mitigated. The reduction in infections would contribute to faster growth of animals to market size and lower veterinary costs for farmers who raised such disease-resistant animals.

The cassette is also useful to transform cells removed from a diseased human patient or animal, so that upon re-introduction into the patient, disease resistance may be enhanced or a particular disease treated. For example, tumor-infiltrating lymphocytes (TILs) can be recovered from a patient's own tumor, transfected in vitro with the cassette, and reintroduced into the host. TILs selectively migrate into tumor tissue and are known to produce high levels of IL-2. Amphipathic peptides and lytic peptide analogues are known to have selective cytocidal activity against tumor cells. Various amphipathic peptides and lytic peptide analogues are known to differ in their effectiveness against fungi, protozoa, and tumor cells. For example, melittin is believed to be particularly effective against tumor cells and thus may be preferred for transfection of TILs.

An advantage of the cassette is that, since it provides its own regulating sequences, the probability of success using random integration techniques is generally high. Further, the types of regulating sequences used ensure that the expression of the amphipathic peptide or lytic peptide analogue is substantially limited to circumstances where it is desirable, e.g. conditions where an infection or a wound exists. Amphipathic peptide expression is further limited to certain cell types which are targeted to the infection or wound site. Injury to the host by production of the amphipathic peptide when it is not needed, is avoided.

---

What is claimed is:

1. A DNA cassette constructed to express an amphipathic peptide, the DNA cassette comprising:
   a first segment encoding an amphipathic peptide, wherein said amphipathic peptide has less than 40 amino acids in length and causes lysis in bacterial, protozoal, and virally infected cells; and
   a promoter segment linked upstream to regulate the expression of said first segment, wherein said promoter segment is isolated from a milk-specific gene selected from the group consisting of: alpha-S1casein, alpha-S2-casein, beta casein, kappa casein, beta lactoglobulin, and alpha lactalbumin, and said promoter segment is an inducible promoter.

2. The cassette of claim 1, wherein said promoter segment encodes a 5' promoter region which normally cis-regulates expression of a milk-specific protein-encoding gene native to a mammal from which said promoter segment was isolated.

3. The cassette of claim 2, which further includes a 3' regulatory segment located downstream of said first segment, said 3' regulatory segment derived from a 3' regulatory region of a milk-specific protein gene native to a mammal from which said promoter segment was isolated.

4. The cassette of claim 2, wherein said protein-encoding gene encodes beta casein, alpha-S1-casein, or beta lactoglobulin.

5. The cassette of claim 2, wherein said first segment encodes an amphipathic peptide selected from the group consisting of: Shiva1, Shiva-2, Shiva-6, Shiva-7, Shiva-9, Hecate-1, Hecate-2, Hecate-3, SB-37, AP-7, Flak-1, and Manitou-1.

6. The cassette of claim 2, which further includes an additional amphipathic peptide encoding gene adjacently linked in reading frame to said first segment.

7. The cassette of claim 2, further including a fusion peptide-encoding segment located adjacent to said first segment for transcription and translation therewith to form a fusion product, said fusion peptide-encoding segment encoding a peptide which renders said fusion product non-toxic.

8. The cassette of claim 7, wherein said fusion peptide-encoding segment encodes a peptide selected from the group consisting of: a chain of six or more histidine residues; green fluorescent protein; streptavidin tag peptide; beta galactosidase; trpE; beta casein; alpha-S1-casein; alpha-S2-casein; beta-lactoglobulin; kappa-casein; alpha-lactalbumin.

9. The cassette of claim 2, which has the sequence of nucleotides nos. 127–4586 of SEQ ID Nos. 5 or 6 in upstream reading frame relationship to a sequence encoding an amphipathic peptide.

10. The cassette of claim 2, which has the sequence of SEQ ID Nos. 5 or 6.

11. The cassette of claim 2, further including a marker segment encoding a selectable marker operably linked downstream of said first segment.

12. The cassette of claim 1, wherein said regulatory segment has a sequence which codes on expression for a protein selected from the group consisting of: interleukin-2 and interleukin-12.

13. The cassette of claim 12, wherein said amphipathic peptide is selected from the group consisting of: SB-37, cecropin B, Shiva-1, Shiva-2, Shiva-3, Shiva-4, Shiva-5, Shiva-6, Shiva-7, Shiva-8, Shiva-9, Shiva-10, melittin, Anubis-1, -2, or -3, Hecate-1, -2, or -3, Manitou-1, Flak1, and Ap-1.

* * * * *

SEQUENCE LISTING ( 1 ) GENERAL INFORMATION:

( i i i ) NUMBER OF SEQUENCES: 32

( 2 ) INFORMATION FOR SEQ ID NO:1:

( i ) SEQUENCE CHARACTERISTICS:
( A ) LENGTH: 25 base pairs
( B ) TYPE: nucleic acid
( C ) STRANDEDNESS: double
( D ) TOPOLOGY: linear ( i i ) MOLECULE TYPE: DNA (genomic)

( v i ) ORIGINAL SOURCE:
( A ) ORGANISM: Mouse
( B ) STRAIN: 3T3 Swiss albino ( x i ) SEQUENCE DESCRIPTION: SEQ ID NO:1:

AGTCGACAAC GACAAAATAG TACCT 25

( 2 ) INFORMATION FOR SEQ ID NO:2:

( i ) SEQUENCE CHARACTERISTICS:
( A ) LENGTH: 25 base pairs
( B ) TYPE: nucleic acid
( C ) STRANDEDNESS: double
( D ) TOPOLOGY: linear ( i i ) MOLECULE TYPE: DNA (genomic)

( v i ) ORIGINAL SOURCE:
( A ) ORGANISM: Mouse
( B ) STRAIN: 3T3 Swiss albino ( x i ) SEQUENCE DESCRIPTION: SEQ ID NO:2:

TAGATCTTGC GCTGTTGACA AGGAG 25

( 2 ) INFORMATION FOR SEQ ID NO:3:

( i ) SEQUENCE CHARACTERISTICS:
( A ) LENGTH: 932 base pairs
( B ) TYPE: nucleic acid
( C ) STRANDEDNESS: double
( D ) TOPOLOGY: linear ( i i ) MOLECULE TYPE: DNA (genomic)

( v i ) ORIGINAL SOURCE:
( A ) ORGANISM: Mouse
( B ) STRAIN: 3T3 Swiss albino ( x i ) SEQUENCE DESCRIPTION: SEQ ID NO:3:

| | | | | | |
|---|---|---|---|---|---|
| GTAAAACGAC | GGCCAGTGCC | AAGCTTGCAT | GCCTGCAGGT | CGACTCTAGA | GGATCCCCAG | 60 |
| TCGACAACGA | CAAAATAGTA | CCTCAAGCTC | AACAAGCATT | TTAGGTGTCC | TTAGCTTACT | 120 |
| ATTTCTCTGG | CTAACTGTAT | GAAGCCATCT | ATCACCCTGT | GTGCAATTAG | CTCATTGTGT | 180 |
| AGATAAGAAG | GTAAAACCAT | CTTGAAACAG | GAAACCAATA | TCCTTCCTGT | CTAATCAACA | 240 |
| AATCTAAAAG | ATTTATTCTT | TTCATCTATC | TCCTCTTGCG | TTTGTCCACC | ACAACAGGCT | 300 |
| GCTTACAGGT | TCAGGATGGT | TTTGACAAAG | AGAACATTTT | CATGAGTTAC | TTTTGTGTCT | 360 |
| CCACCCCAAA | GAGGAAAATT | TGTTTCATAC | AGAAGGCGTT | CATTGTATGA | ATTAAAACTG | 420 |
| CCACCTAAGT | GTGGGCTAAC | CCGACCAAGA | GGGATTTCAC | CTAAATCCAT | TCAGTCAGTG | 480 |
| TATGGGGGTT | TAAAGAAATT | CCAGAGAGTC | ATCAGAAGAG | GAAAACAAA  | GGTAATGCTT | 540 |
| TCTGCCACAC | AGGTAGACTC | TTTGAAAATA | TGTGTAATAT | GTAAACATC  | GTGACACCCC | 600 |
| CATATTATTT | TTCCAGCATT | AACAGTATAA | ATTGCCTCCC | ATGCTGAAGA | GCTGCCTATC | 660 |
| ACCCTTGCTA | ATCACTCCTC | ACAGTGACCT | CAAGTCCTGC | AGGCATGTAC | AGCATGCAGC | 720 |
| TCGCATCCTG | TGTCACATTG | ACACTTGTGC | TCCTTGTCAA | CAGCGCAAGA | TCTACCATGC | 780 |

| | | | | | | |
|---|---|---|---|---|---|---|
| CGCGCTGGCG | TCTGTTCCGC | CGTATCGACC | GTGTTGGCAA | ACAGATCAAA | CAGGGTATCC | 840 |
| TGCCGTGCTG | GCCCGGCTAT | CGCTCTGGTT | GGCGACGCCC | GCGCAGTTGG | TTGAGAATTC | 900 |
| GTAATCATGG | TCATAGCTGT | TTCCTGTGTG | AA | | | 932 |

( 2 ) INFORMATION FOR SEQ ID NO:4:

( i ) SEQUENCE CHARACTERISTICS:
        ( A ) LENGTH: 21 base pairs
        ( B ) TYPE: nucleic acid
        ( C ) STRANDEDNESS: double
        ( D ) TOPOLOGY: unknown ( i i ) MOLECULE TYPE: DNA (genomic)

( i i i ) HYPOTHETICAL: NO ( v i ) ORIGINAL SOURCE:
        ( A ) ORGANISM: Streptomyces fradiae ( x i ) SEQUENCE DESCRIPTION: SEQ ID NO:4:

| | | |
|---|---|---|
| CCACCATGAT | ATTCGGCAAG C | 2 1 |

( 2 ) INFORMATION FOR SEQ ID NO:5:

( i ) SEQUENCE CHARACTERISTICS:
        ( A ) LENGTH: 11093 base pairs
        ( B ) TYPE: nucleic acid
        ( C ) STRANDEDNESS: double
        ( D ) TOPOLOGY: Not Relevant ( i i ) MOLECULE TYPE: other nucleic acid
        ( A ) DESCRIPTION: /desc = "Construct comprising
            portions of Bos taurus beta casein gene and genes
            encoding amphipathic peptide and green fluorescent
            protein"

( i i i ) HYPOTHETICAL: YES ( i v ) ANTI-SENSE: NO ( i x ) FEATURE:
        ( A ) NAME/KEY: exon
        ( B ) LOCATION: 1801..1834
        ( D ) OTHER INFORMATION: /product= "beta casein exon 1"

( i x ) FEATURE:
        ( A ) NAME/KEY: exon
        ( B ) LOCATION: 3780..3832
        ( D ) OTHER INFORMATION: /product= "beta casein exon 2"

( i x ) FEATURE:
        ( A ) NAME/KEY: TATA_signal
        ( B ) LOCATION: 1766..1773

( i x ) FEATURE:
        ( A ) NAME/KEY: exon
        ( B ) LOCATION: 4567..4590
        ( D ) OTHER INFORMATION: /product= "portion of beta casein
            exon 3"

( i x ) FEATURE:
        ( A ) NAME/KEY: 5'UTR
        ( B ) LOCATION: 127..1800
        ( D ) OTHER INFORMATION: /function= "5'flanking regulatory
            region of bovine beta casein gene"

( i x ) FEATURE:
        ( A ) NAME/KEY: mat_peptide
        ( B ) LOCATION: 4587..5310
        ( D ) OTHER INFORMATION: /product= "Green fluorescent
            protein"

( i x ) FEATURE:
        ( A ) NAME/KEY: mat_peptide
        ( B ) LOCATION: 5320..5449

( D ) OTHER INFORMATION: /product= "Shiva-1 coding sequence"

( i x ) FEATURE:
  ( A ) NAME/KEY: polyA_signal
( B ) LOCATION: 7630..7635
( D ) OTHER INFORMATION: /standard_name= "Bovine beta casein 3'region, in exon 9"

( x i ) SEQUENCE DESCRIPTION: SEQ ID NO:5:

```
TAGTTATTAA TAGTAATCAA TTACGGGGTC ATTAGTTCAT AGCCCATATA TGGAGTTCCG    60
CGTTACATAA CTTACGGTAA ATGGCCCGCC TGGCTGACCG CCCAACGACC CCCGCCCATT   120
GACGTCGTCA TTAGGAAATT CTCTGTTTAT TGCACAATAT GTAAAGCATC TTCCTGAGAA   180
AAGGGAAATG TTGAATGGGA AGGACATGCT TTCTTTTGTA TTCCTTTTCT CAGAAATCAC   240
ACTTTTTTGC CTGTGGCCTT GGCAACCAAA AGCTAACACA TAAAGAAAGG CATATGAAGT   300
AGCCAAGGCC TTTTCTAGTT ATATCTATGA CACTGAGTTC ATTTCATCAT TTATTTTCCT   360
GACTTCCTCC TGGGCCATAT GAGCAGTCTT AGAATGAATA TTAGCTGAAT AATCCAAATG   420
CATAGTAGAT GTTGATTTGG GTTTTCTAAG CAATACAAGA CTTCTATGAC AGTGAGATGT   480
ATTACCATCC AACACACATC TCAGCATGAT ATAAATGTAA GGTATATTGT GAAGAAAAAT   540
TATCAATTAT GTCAAAGTGC TTACTTTAGA AGATCATCTA TCTGTCCCAA AGCTGTGAAT   600
ATATATATTG AACATAATTA ATAGACGAAA CAAACCTTGT AAAAATGAGT AGTGTAAAAT   660
ACAACTACAT TTATGAACAT CTATCACTAA AGAGGCAAAG AAAGTTGAGG ACTGCTTTTG   720
TAAATGGGCT CTTATTAATG AAAAGTACTT TTGAGGTCTG GCTTAGACTC TATTGTAGTA   780
CTTATGGTAA GACCCTCCTC TTGTCTGGGC TTTCATTTTC TTTCTTCCTT CCCTCATTTG   840
CCCTTCCATG AATACTAGCT GATAAACATT GACTCACTAT AAAAGATATG AGGCCAAACT   900
TGAGCTGTCC ATTTTAATAA ATCTGTATAA ATAATATTTG TTCTACAGAA GTATCTCTAA   960
ATAAATGTAC TTTCTCTCTT AAAATCCCTC AACAAATCCC CACTATCTAG AGAATAAGAT  1020
TGACATTCCC TGGAGTCACA GCATGCTTTG TCTGCCATTA TCTGACCCCT TTCTCTTTCT  1080
CTCTTCTCAC CTCCATCTAC TCCTTTTTCC TTGCAATACA TGACCCAGAT TCACTGTTTG  1140
ATTTGGCTTG CATGTGTGTG TGCTGAGTTG TGTCTCACTC TTGTCAACCC CATGAATGAC  1200
AGTCCACCAG GCTCCACTAT TTCCAGTTAA GAATACTGGA GTGGATTGTG TTTCCTACTT  1260
CATTTGATTA ATTTAGTGAC TTTTTAAATT TTTTTCCATA TTCAGGAGGC TATTCTTTCC  1320
TTTTAGTCTA TACTGTCTTC GCTCTTCAGG TCTAAGCTAT CATCATGTGC TTGTTAGCTT  1380
GTTTCTTTCT CCATTATAGC ATAAACACTA ACAACTATTC AGGTTAGCAT GAGATTGTGT  1440
TCTTTGTGTG GCCTGTGTAT TTCTGGTGTG TATTAGAATT TACCCCAAGA TCTCAAAGAC  1500
CCACCGAATA CTAAAGAGAC CTCATTGTAG TTACAATAAT TTGGGGACTG GGCCAAAACT  1560
TCCGTGTGTC CCAGCCAAGG TCTGTAGCTA CTGGACAATT TAATTTCCTT TATCAGATTG  1620
TGAATTATTC CCTTTAAAAT GCTCCCCAGA ATTTTTGGGG ACAGAAAAAT AGGAAGAATT  1680
CATTTTCTAA TCATGCAGAT TTCTAGGAAT TCAAATCCAC TATTGGTTTT ATTTCAAACC  1740
ACAAAATTAG CATGCCATTA AATACTATAT ATAAACAACC ACAAAATCAG ATCATTATCC  1800
ATTCAGCTCC TCCTTCACTT CTTGTCCTCT ACTTTGGAAA AAAGGTAAGA ATCTCAGATA  1860
TAATTTCATT GTATCTGCTA CTCATCTTTA TTTCAGACTA GGTTAAAATG TAGAAAGAAC  1920
ATAATTGCTT AAAATAGATC TTAAAAATAA GGATGTTTAA GATAAAGTTT ACAGTATTTT  1980
CAGCAAATTT GTTAAAAAAT AGAAGCAACT ATAAAGATTT GTAACAGTGG TTGCTATTTT  2040
CTTTACCACG AGACTAGTTA ACAGGCTGTA TTAAAAGATC TTTTCTTGAA TTAAATATTT  2100
```

```
TCAATTTGAT   TAAACATACC   TCAGCCATAA   AGGCAAGCAC   ATTTAATTTA   TACTATGGGA   2160
ATTTGAATAA   TTGTTACTGA   AGAAGCTCTA   CCAACAAAAA   GTTTATAGAG   CTAGCATATT   2220
TAGTCAAGAG   ATAAAGAGGG   TTGTTAGGAT   ACATGTGCTA   TTTGAAAGGT   ATTTATAAAA   2280
GAAGAGTATA   TTTATTAAAA   TTGCTCAGAA   CATCCAAATT   TCAAGTTTAT   CATTTATCTT   2340
ACAATATTTC   AAAAATATTA   AAATAGATAC   ATGAAATACA   GAAGTAAATT   AAAGAGAAAG   2400
TATTTTATTT   TGTAAAAAAA   AATTCTAGGT   TGGACAGGGA   GTACCAGGAA   ACAAAAAACA   2460
ATGAAAAATG   TGATCTGACA   GAAATTATAG   CTCAAAGTAT   AGTAGTCAGT   AATGAAATGG   2520
CTTAAAAATT   GGCATATAAA   ATGCTAATTA   TAAAATAAAC   AAAATGTAAT   AATACCCTCC   2580
CTACATGTAA   TGAACTCTGA   GTATTATACT   CTTTTTTGAA   GTCTTGACAA   TGAAAATTTA   2640
TTTAGACTTT   TATAGACATC   TTGGATAAAG   TAAAACAAAT   TACGAATTAG   CATCCATGAG   2700
AAAAATATAG   AAAAATTTCT   TAATGTAGTT   TGCAAATCTG   GGGATTGAAG   ATGTGTGTCA   2760
AGAGATTGTG   ATGGCAGACA   TTTTTTTTCA   GACTATAAAA   TGCACAAACA   ACCATTTAAT   2820
ACATTTGGT    CAAAAATAGT   ATGTATTTTA   TTTTATGCTA   CAGGAGAGTA   GTCTAAAGTA   2880
GGACTGGGCA   GAGATCTGAC   ACCCTGGTAA   TCACCGAGAG   ATAGTACACA   GTCTCTGTAG   2940
AGAAAATAAG   CATAGTGTAT   GATCTCTAAA   ATTATGTGGA   CAAAGGGGAG   ATAACATTAG   3000
GCATGTGGGG   ATGAAGACTG   AGTACAGAAG   AACAATCTAG   TCAGTCCAAG   AAAACATGTG   3060
GATCAATGGA   ACAAATAGAA   GAAATGCTAA   AATGAAACAG   AAGTCTTACT   GGAAATAAAA   3120
GATATGAGGA   AGACAAACAT   TCATGAAAAT   CACTTAGTTT   AGTAGAGAAA   AGATAAAAAT   3180
AAAGTATTAC   CTTCTTCTTC   ATATACATTG   TTTGATCAGA   TGCCCCTCAA   TAAAACTGAG   3240
TCTCCAACAG   AACTGAAACT   TTAATATTTT   GTTCACTGCT   CTAATCCCAG   AATCTAAGAC   3300
ATATCTGGCA   ATAAAAATTA   ATAAATAAAT   ATTTTAATA    AGTAAATCAA   TCACTTAATT   3360
TTTCTGTAAG   TATCTGTAAC   TTCTCTTCTG   TCTTTCCAAA   AAACACTCAT   AAGTACTGTG   3420
AATAAGATGA   AAAGAGTGAA   ATAAGATATA   GGCTGTTAGC   TGAAAACATC   TGGATGGCTG   3480
GCAGTGAAAC   ATTAACTTGA   AATGTAAGAT   TAATGAGTAA   TAGTAAATTT   TAACCTTGGC   3540
CGTATGATAA   AATGTCTATT   AATATTTTTC   TAAAATACAG   GGCTTTTTGT   TTTTGCCATG   3600
AGGTTTGCAG   GATCTTGGTT   CCCTGATGAG   GGATCAAACC   TGGGCTCCCC   TGGAAGCACG   3660
GAGTCTTAGA   TATTTGTATT   ATACACTATC   TTTGGTTTCT   TTTAAAGGGA   AGTAATTCTA   3720
CTTAAATAAG   AAAATAGATT   GACAAGTAAT   ACACTATTTC   CTCATCTTCC   CATTCCCAGG   3780
AATTGAGAGC   CATGAAGGTC   CTCATCCTTG   CCTGCCTGGT   GGCTCTGGCC   CTTGCAAGAG   3840
AGGTAAATAC   AGAAAAAATG   TTGAAATAAA   TAAGACTAGT   ACTATCTGCT   ATGTGTAGAA   3900
AATTCATTAC   CAACATTGTA   AATGTATAAA   TAATGCACAA   TCTCAGATTT   TTTTTGAATG   3960
CTAAGAAAGT   CATTTACGTT   CATCCACTAT   CTCAGTAGTA   TCCTATGGGA   CCACAAGTCT   4020
GAGTCTAGTG   CTTTCTATAG   TATTGTACCA   TCTGTACCAT   CAATCCCTAA   AGAAAAAAGA   4080
AAATAAACCA   ATAAGCAACA   GACTAACAAG   AAGGAACACA   GATAAGAACA   AAAAGTGAGT   4140
AATATTGCAT   AAATACAATT   GCATGCATAT   ACAATCTAGA   TAAATATATC   TTATTCCAGT   4200
GATGAAATAT   TTGTATCCCT   TACTGTAGAG   TGCTAGGTTT   AGCTGTGTCT   ATTCAACACA   4260
GGATGATACT   CCAGAGGATG   GTATATCAGA   CAACAATAAT   AAATATGTTC   ATAATTATAA   4320
TAAAAAGTGT   TCAGTAAAAA   TTAAAATAAC   TCCTTTTCTG   TTACCCATAA   AAACTCTTCA   4380
TTAAAGTAAA   ACAAAAATAT   ACTAATGAAA   GTTACTAAAT   TTAAAAGACT   CTCAAAAGAC   4440
ATATAACATT   TTTATTTTTC   AGATTTGTGA   AATAGATAGC   TCTGAATAAA   GCAAGTAAAA   4500
```

```
ATTAGGTAGG AAAATATTTA ATAATGAGTT GACTGTGGGA ACTAAAGTGT TTTTTTTCT    4560
CTTTAGCTGG AAGAACTCAA TGTACCGGTC GCCACCATGG GTAAAGGAGA AGAACTTTTC   4620
ACTGGAGTTG TCCCAATTCT TGTTGAATTA GATGGTGATG TTAATGGGCA CAAATTTTCT   4680
GTCAGTGGAG AGGGTGAAGG TGATGCAACA TACGGAAAAC TTACCCTTAA ATTTATTTGC   4740
ACTACTGGAA AACTACCTGT TCCATGGCCA ACACTTGTCA CTACTTTCTC TTATGGTGTT   4800
CAATGCTTTT CAAGATACCC AGATCATATG AAACGGCATG ACTTTTTCAA GAGTGCCATG   4860
CCCGAAGGTT ATGTACAGGA AGAACTATA TTTTTCAAAG ATGACGGGAA CTACAAGACA    4920
CGTGCTGAAG TCAAGTTTGA AGGTGATACC CTTGTTAATA GAATCGAGTT AAAAGGTATT   4980
GATTTTAAAG AAGATGGAAA CATTCTTGGA CACAAATTGG AATACAACTA TAACTCACAC   5040
AATGTATACA TCATGGCAGA CAAACAAAAG AATGGAATCA AAGTTAACTT CAAAATTAGA   5100
CACAACATTG AAGATGGAAG CGTTCAACTA GCAGACCATT ATCAACAAAA TACTCCAATT   5160
GGCGATGGCC CTGTCCTTTT ACCAGACAAC CATTACCTGT CCACACAATC TGCCCTTTCG   5220
AAAGATCCCA ACGAAAAGAG AGACCACATG GTCCTTCTTG AGTTTGTAAC AGCTGCTGGG   5280
ATTACACATG GCATGGATGA ACTATACAAG TCCGGACTCA GATCTACCAT GCCGCGCTGG   5340
CGTCTGTTCC GCCGTATCGA CCGTGTTGGC AAACAGATCA AACAGGGTAT CCTGCGTGCT   5400
GGCCCGGCTA TCGCTCTGGT TGGCGACGCC CGCGCAGTTG GTTGAGAATT CTGCAGTCGA   5460
CGGTACCAGG ATAAAATCCA CCCCTTTGCC CAGACACAGT CTCTAGTCTA TCCCTTCCCT   5520
GGACCCATCC ATAACAGCCT CCCACAAAAC ATCCCTCCTC TTACTCAAAC CCCTGTGGTG   5580
GTGCCGCCTT TCCTTCAGCC TGAAGTAATG GGAGTCTCCA AAGTGAAGGA GGCTATGGCT   5640
CCTAAGCACA AAGAAATGCC CTTCCCTAAA TATCCAGTTG AGCCCTTTAC TGAAAGCCAG   5700
AGCCTGACTC TCACTGATGT TGAAAATCTG CACCTTCCTC TGCCTCTGCT CCAGTCTTGG   5760
ATGCACCAGC CTCACCAGCC TCTTCCTCCA ACTGTCATGT TTCCTCCTCA GTCCGTGCTG   5820
TCCCTTTCTC AGTCCAAAGT CCTGCCTGTT CCCCAGAAAG CAGTGCCCTA TCCCCAGAGA   5880
GATATGCCCA TTCAGGCCTT TCTGCTGTAC CAGGAGCCTG TACTCGGTCC TGTCCGGGGA   5940
CCCTTCCCTA TTATTGTAAG TCTAAATTTA CTAACTGTGC CTGTTTAACT TCTGATGTTT   6000
GTATGATATT CGAGTAATTA AGAGTCCTAT AAAAAAATGA ATAATGAATG GTTCCAAAAT   6060
AAGCATAGCT GAGATTAATG ATTGTCAGCA TTAGTTATAA ATAGAATAAG CTGGAGAACC   6120
TTCACCTCCC CTCCACCACC AGATCTCAAT GTCTAGGCTT ACCCGTGGAG ATTCTGATGT   6180
AATTGTTCTT TCTATGTAGA AGAAACTTAT TGGGAAGAAA TAATATAATG GACTATGATT   6240
TAATTGGTCT GTTGAGAACC AATTAAATTA GATGAAAGCG ATTAAGTACA ATAAAGCCAA   6300
AATTGAATTT GATAATCTCA TTTGGCTAAG AATAACAAAC CTAAGAAGGT TTGCTATTTT   6360
CTACAATTTT GAAGTTCTCC TTATGCACAA TTATTTCACC ACATGACTCA TTTCACATCG   6420
TGTTTTTGAT ATATGAGCAT ATGAGGGAAA AATACTGAGA TGCTTATTTC AATACTCAGG   6480
GAAAATTTAT TGCCAAAAGG CAAGAAATGT ATAATTCATT CACTTATTTT ATTTTATTAT   6540
TTTTTTTATT TTAAGGTCT AAGAGGATTT CAAAGTGAAT GCCCCTCCT CACTTTTGGT     6600
AAGCTTTAGG ATATTGGAGG CAGACTGATC ATTTTTATAG TTAATATCTT TTACATTTCA   6660
TTTTCCTGGA TAAGCCCCAA TAGTAGCAAT TCCATCAGT GTACCAGCTT AAAGATTAAT    6720
TATAAATTTA TTTTCAATGA TTGACTGTTA TTTACTGGCC TGAAATTATG TATCTGTTAT   6780
ATTTCAAATA ATGCAAAACT GTATATATAT GGTGTTTACA GATTTGATTG GTTTCTTTC   6840
AATAGCCTAT ATCCTTATTA TTGATTGTCA TCATTTATAG AAAAAACTGA AAATAATTTC   6900
```

```
TTATACTTTT ATGTAAACCT GTTAGAGCTT ATTTTAAAGA TCAACTGCAT TCACATTTCT    6960
AATCTAGTCA TTATGAGCTT CAATAGTTTT ATCTCACTTA AAATATATAT ATTGTCTTTT    7020
AATTCATGAG TCAAAATACA ATCTCACAGT CCAGATATGG GACTTAAAAG GGGGATAGAA    7080
TATAGTTTTG ATATTCTTAA CAATACACAT CCTTTTGTGA TCATGATTCA GCAGACATTT    7140
AATAAAATGA TTCCAAGTAA GCCGATGTTT GGTCCTAGAG GAATTTTTAT AACCTTTAAG    7200
AGAAGGCATA GCATGGTGTT TTTGTAATAA GATTTCTTTT ATGAAAAAGT CACACCAAAA    7260
TTGCAAATGG GGGTGAGATG AAGAGTTATA ACATATAACT AAATCTATGT TTGTTCTCTA    7320
TTCCACAGAA TTGACTGCGA CTGGAAATAT GGCAACTTTT CAATCCTTGC ATCATGTTAC    7380
TAAGATAATT TTTAAATGAG TATACATGGA ACAAAAAATG AAACTTTATT CCTTTATTTA    7440
TTTTATGCTT TTTCATCTTA ATTTGAATTT GAGTCATAAA CTATATATTT CAAAATTTTA    7500
ATTCAACATT AGCATAAAAG TTCAATTTTA ACTTGGAAAT ATCATGAACA TATCAAAATA    7560
TGTATAAAAA TAATTTCTGG AATTGTGATT ATTATTTCTT TAAGAATCTA TTTCCTAACC    7620
AGTCATTTCA ATAAATTAAT CCTTAGGCAT ATTTAAGTTT TCTTGTCTTT ATTATATTTT    7680
TTTTAATGAA ATTGGTCTCT TTATTGTTAA CTTAAATTTA TCTTTGATGT TAAAAGAGC    7740
TGTGGAAAAT TAAAATTGGA GGATCTAGAT AACTGATCAT AATCAGCCAT ACCACATTTG    7800
TAGAGGTTTT ACTTGCTTTA AAAACCTCC CACACCTCCC CCTGAACCTG AAACATAAAA    7860
TGAATGCAAT TGTTGTTGTT AACTTGTTTA TTGCAGCTTA TAATGGTTAC AAATAAAGCA    7920
ATAGCATCAC AAATTTCACA AATAAAGCAT TTTTTCACT GCATTCTAGT TGTGGTTTGT    7980
CCAAACTCAT CAATGTATCT TAACGCGTAA ATTGTAAGCG TTAATATTTT GTTAAAATTC    8040
GCGTTAAATT TTTGTTAAAT CAGCTCATTT TTTAACCAAT AGGCCGAAAT CGGCAAAATC    8100
CCTTATAAAT CAAAAGAATA GACCGAGATA GGGTTGAGTG TTGTTCCAGT TTGGAACAAG    8160
AGTCCACTAT TAAAGAACGT GGACTCCAAC GTCAAAGGGC GAAAACCGT CTATCAGGGC    8220
GATGGCCCAC TACGTGAACC ATCACCCTAA TCAAGTTTTT TGGGGTCGAG GTGCCGTAAA    8280
GCACTAAATC GGAACCCTAA AGGGAGCCCC CGATTTAGAG CTTGACGGGG AAAGCCGGCG    8340
AACGTGGCGA GAAAGGAAGG GAAGAAAGCG AAAGGAGCGG GCGCTAGGGC GCTGGCAAGT    8400
GTAGCGGTCA CGCTGCGCGT AACCACCACA CCCGCCGCGC TTAATGCGCC GCTACAGGGC    8460
GCGTCAGGTG GCACTTTTCG GGGAAATGTG CGCGGAACCC CTATTTGTTT ATTTTTCTAA    8520
ATACATTCAA ATATGTATCC GCTCATGAGA CAATAACCCT GATAAATGCT TCAATAATAT    8580
TGAAAAAGGA AGAGTCCTGA GGCGGAAAGA ACCAGCTGTG GAATGTGTGT CAGTTAGGGT    8640
GTGGAAAGTC CCCAGGCTCC CCAGCAGGCA GAAGTATGCA AAGCATGCAT CTCAATTAGT    8700
CAGCAACCAG GTGTGGAAAG TCCCCAGGCT CCCCAGCAGG CAGAAGTATG CAAAGCATGC    8760
ATCTCAATTA GTCAGCAACC ATAGTCCCGC CCCTAACTCC GCCCATCCCG CCCCTAACTC    8820
CGCCCAGTTC CGCCCATTCT CCGCCCCATG GCTGACTAAT TTTTTTTATT TATGCAGAGG    8880
CCGAGGCCGC CTCGGCCTCT GAGCTATTCC AGAAGTAGTG AGGAGGCTTT TTTGGAGGCC    8940
TAGGCTTTTG CAAAGATCGA TCAAGAGACA GGATGAGGAT CGTTTCGCAT GATTGAACAA    9000
GATGGATTGC ACGCAGGTTC TCCGGCCGCT TGGGTGGAGA GGCTATTCGG CTATGACTGG    9060
GCACAACAGA CAATCGGCTG CTCTGATGCC GCCGTGTTCC GGCTGTCAGC GCAGGGGCGC    9120
CCGGTTCTTT TTGTCAAGAC CGACCTGTCC GGTGCCCTGA ATGAACTGCA AGACGAGGCA    9180
GCGCGGCTAT CGTGGCTGGC CACGACGGGC GTTCCTTGCG CAGCTGTGCT CGACGTTGTC    9240
ACTGAAGCGG GAAGGGACTG GCTGCTATTG GGCGAAGTGC CGGGGCAGGA TCTCCTGTCA    9300
```

| | | | | | |
|---|---|---|---|---|---|
| TCTCACCTTG | CTCCTGCCGA | GAAAGTATCC | ATCATGGCTG | ATGCAATGCG | GCGGCTGCAT | 9360 |
| ACGCTTGATC | CGGCTACCTG | CCCATTCGAC | CACCAAGCGA | AACATCGCAT | CGAGCGAGCA | 9420 |
| CGTACTCGGA | TGGAAGCCGG | TCTTGTCGAT | CAGGATGATC | TGGACGAAGA | GCATCAGGGG | 9480 |
| CTCGCGCCAG | CCGAACTGTT | CGCCAGGCTC | AAGGCGAGCA | TGCCCGACGG | CGAGGATCTC | 9540 |
| GTCGTGACCC | ATGGCGATGC | CTGCTTGCCG | AATATCATGG | TGGAAAATGG | CCGCTTTTCT | 9600 |
| GGATTCATCG | ACTGTGGCCG | GCTGGGTGTG | GCGGACCGCT | ATCAGGACAT | AGCGTTGGCT | 9660 |
| ACCCGTGATA | TTGCTGAAGA | GCTTGGCGGC | GAATGGGCTG | ACCGCTTCCT | CGTGCTTTAC | 9720 |
| GGTATCGCCG | CTCCCGATTC | GCAGCGCATC | GCCTTCTATC | GCCTTCTTGA | CGAGTTCTTC | 9780 |
| TGAGCGGGAC | TCTGGGGTTC | GAAATGACCG | ACCAAGCGAC | GCCCAACCTG | CCATCACGAG | 9840 |
| ATTTCGATTC | CACCGCCGCC | TTCTATGAAA | GGTTGGGCTT | CGGAATCGTT | TTCCGGGACG | 9900 |
| CCGGCTGGAT | GATCCTCCAG | CGCGGGATC | TCATGCTGGA | GTTCTTCGCC | CACCCTAGGG | 9960 |
| GGAGGCTAAC | TGAAACACGG | AAGGAGACAA | TACCGGAAGG | AACCCGCGCT | ATGACGGCAA | 10020 |
| TAAAAAGACA | GAATAAAACG | CACGGTGTTG | GGTCGTTTGT | TCATAAACGC | GGGGTTCGGT | 10080 |
| CCCAGGGCTG | GCACTCTGTC | GATACCCCAC | CGAGACCCCA | TTGGGGCCAA | TACGCCCGCG | 10140 |
| TTTCTTCCTT | TTCCCCACCC | CACCCCCCAA | GTTCGGGTGA | AGGCCCAGGG | CTCGCAGCCA | 10200 |
| ACGTCGGGGC | GGCAGGCCCT | GCCATAGCCT | CAGGTTACTC | ATATATACTT | TAGATTGATT | 10260 |
| TAAAACTTCA | TTTTTAATTT | AAAAGGATCT | AGGTGAAGAT | CCTTTTTGAT | AATCTCATGA | 10320 |
| CCAAAATCCC | TTAACGTGAG | TTTTCGTTCC | ACTGAGCGTC | AGACCCCGTA | GAAAAGATCA | 10380 |
| AAGGATCTTC | TTGAGATCCT | TTTTTTCTGC | GCGTAATCTG | CTGCTTGCAA | ACAAAAAAAC | 10440 |
| CACCGCTACC | AGCGGTGGTT | TGTTTGCCGG | ATCAAGAGCT | ACCAACTCTT | TTTCCGAAGG | 10500 |
| TAACTGGCTT | CAGCAGAGCG | CAGATACCAA | ATACTGTCCT | TCTAGTGTAG | CCGTAGTTAG | 10560 |
| GCCACCACTT | CAAGAACTCT | GTAGCACCGC | CTACATACCT | CGCTCTGCTA | ATCCTGTTAC | 10620 |
| CAGTGGCTGC | TGCCAGTGGC | GATAAGTCGT | GTCTTACCGG | GTTGGACTCA | AGACGATAGT | 10680 |
| TACCGGATAA | GGCGCAGCGG | TCGGGCTGAA | CGGGGGGTTC | GTGCACACAG | CCCAGCTTGG | 10740 |
| AGCGAACGAC | CTACACCGAA | CTGAGATACC | TACAGCGTGA | GCTATGAGAA | AGCGCCACGC | 10800 |
| TTCCCGAAGG | GAGAAAGGCG | GACAGGTATC | CGGTAAGCGG | CAGGGTCGGA | ACAGGAGAGC | 10860 |
| GCACGAGGGA | GCTTCCAGGG | GGAAACGCCT | GGTATCTTTA | TAGTCCTGTC | GGGTTTCGCC | 10920 |
| ACCTCTGACT | TGAGCGTCGA | TTTTTGTGAT | GCTCGTCAGG | GGGCGGAGC | CTATGGAAAA | 10980 |
| ACGCCAGCAA | CGCGGCCTTT | TTACGGTTCC | TGGCCTTTTG | CTGGCCTTTT | GCTCACATGT | 11040 |
| TCTTTCCTGC | GTTATCCCCT | GATTCTGTGG | ATAACCGTAT | TACCGCCATG | CAT | 11093 |

( 2 ) INFORMATION FOR SEQ ID NO:6:

( i ) SEQUENCE CHARACTERISTICS:
        ( A ) LENGTH: 8797 base pairs
        ( B ) TYPE: nucleic acid
        ( C ) STRANDEDNESS: double
        ( D ) TOPOLOGY: Not Relevant ( i i ) MOLECULE TYPE: other nucleic acid
        ( A ) DESCRIPTION: /desc = "Construct comprising Bos
        taurus beta casein 5'regulatory region plus genes
        encoding amphipathic peptide and green fluorescent
        protein"

( i i i ) HYPOTHETICAL: YES ( i v ) ANTI-SENSE: NO ( x i ) SEQUENCE DESCRIPTION: SEQ ID NO:6:

-continued

| | | | | | |
|---|---|---|---|---|---|
|TAGTTATTAA|TAGTAATCAA|TTACGGGGTC|ATTAGTTCAT|AGCCCATATA|TGGAGTTCCG| 60
|CGTTACATAA|CTTACGGTAA|ATGGCCCGCC|TGGCTGACCG|CCCAACGACC|CCCGCCCATT| 120
|GACGTCGTCA|TTAGGAAATT|CTCTGTTTAT|TGCACAATAT|GTAAAGCATC|TTCCTGAGAA| 180
|AAGGGAAATG|TTGAATGGGA|AGGACATGCT|TTCTTTTGTA|TTCCTTTCT|CAGAAATCAC| 240
|ACTTTTTTGC|CTGTGGCCTT|GGCAACCAAA|AGCTAACACA|TAAAGAAAGG|CATATGAAGT| 300
|AGCCAAGGCC|TTTTCTAGTT|ATATCTATGA|CACTGAGTTC|ATTTCATCAT|TTATTTTCCT| 360
|GACTTCCTCC|TGGGCCATAT|GAGCAGTCTT|AGAATGAATA|TTAGCTGAAT|AATCCAAATG| 420
|CATAGTAGAT|GTTGATTTGG|GTTTTCTAAG|CAATACAAGA|CTTCTATGAC|AGTGAGATGT| 480
|ATTACCATCC|AACACACATC|TCAGCATGAT|ATAAATGTAA|GGTATATTGT|GAAGAAAAT| 540
|TATCAATTAT|GTCAAAGTGC|TTACTTTAGA|AGATCATCTA|TCTGTCCCAA|AGCTGTGAAT| 600
|ATATATATTG|AACATAATTA|ATAGACGAAA|CAAACCTTGT|AAAAATGAGT|AGTGTAAAAT| 660
|ACAACTACAT|TTATGAACAT|CTATCACTAA|AGAGGCAAAG|AAAGTTGAGG|ACTGCTTTTG| 720
|TAAATGGGCT|CTTATTAATG|AAAAGTACTT|TTGAGGTCTG|GCTTAGACTC|TATTGTAGTA| 780
|CTTATGGTAA|GACCCTCCTC|TTGTCTGGGC|TTTCATTTTC|TTTCTTCCTT|CCCTCATTTG| 840
|CCCTTCCATG|AATACTAGCT|GATAAACATT|GACTCACTAT|AAAGATATG|AGGCCAAACT| 900
|TGAGCTGTCC|ATTTTAATAA|ATCTGTATAA|ATAATATTTG|TTCTACAGAA|GTATCTCTAA| 960
|ATAAATGTAC|TTTCTCTCTT|AAAATCCCTC|AACAAATCCC|CACTATCTAG|AGAATAAGAT| 1020
|TGACATTCCC|TGGAGTCACA|GCATGCTTTG|TCTGCCATTA|TCTGACCCCT|TTCTCTTTCT| 1080
|CTCTTCTCAC|CTCCATCTAC|TCCTTTTTCC|TTGCAATACA|TGACCCAGAT|TCACTGTTTG| 1140
|ATTTGGCTTG|CATGTGTGTG|TGCTGAGTTG|TGTCTCACTC|TTGTCAACCC|CATGAATGAC| 1200
|AGTCCACCAG|GCTCCACTAT|TTCCAGTTAA|GAATACTGGA|GTGGATTGTG|TTTCCTACTT| 1260
|CATTTGATTA|ATTTAGTGAC|TTTTTAAATT|TTTTTCCATA|TTCAGGAGGC|TATTCTTTCC| 1320
|TTTTAGTCTA|TACTGTCTTC|GCTCTTCAGG|TCTAAGCTAT|CATCATGTGC|TTGTTAGCTT| 1380
|GTTTCTTTCT|CCATTATAGC|ATAAACACTA|ACAACTATTC|AGGTAGCAT|GAGATTGTGT| 1440
|TCTTTGTGTG|GCCTGTGTAT|TTCTGGTGTG|TATTAGAATT|TACCCCAAGA|TCTCAAAGAC| 1500
|CCACCGAATA|CTAAAGAGAC|CTCATTGTAG|TTACAATAAT|TTGGGGACTG|GGCCAAAACT| 1560
|TCCGTGTGTC|CCAGCCAAGG|TCTGTAGCTA|CTGGACAATT|TAATTTCCTT|TATCAGATTG| 1620
|TGAATTATTC|CCTTTAAAAT|GCTCCCCAGA|ATTTTGGGG|ACAGAAAAAT|AGGAAGAATT| 1680
|CATTTTCTAA|TCATGCAGAT|TTCTAGGAAT|TCAAATCCAC|TATTGGTTTT|ATTTCAAACC| 1740
|ACAAAATTAG|CATGCCATTA|AATACTATAT|ATAAACAACC|ACAAAATCAG|ATCATTATCC| 1800
|ATTCAGCTCC|TCCTTCACTT|CTTGTCCTCT|ACTTTGGAAA|AAAGGTAAGA|ATCTCAGATA| 1860
|TAATTTCATT|GTATCTGCTA|CTCATCTTTA|TTTCAGACTA|GGTTAAAATG|TAGAAAGAAC| 1920
|ATAATTGCTT|AAAATAGATC|TTAAAAATAA|GGATGTTTAA|GATAAAGTTT|ACAGTATTTT| 1980
|CAGCAAATTT|GTTAAAAAAT|AGAAGCAACT|ATAAAGATTT|GTAACAGTGG|TTGCTATTTT| 2040
|CTTTACCACG|AGACTAGTTA|ACAGGCTGTA|TTAAAAGATC|TTTTCTTGAA|TTAAATATTT| 2100
|TCAATTTGAT|TAAACATACC|TCAGCCATAA|AGGCAAGCAC|ATTTAATTTA|TACTATGGGA| 2160
|ATTGAATAA|TTGTTACTGA|AGAAGCTCTA|CCAACAAAAA|GTTTATAGAG|CTAGCATATT| 2220
|TAGTCAAGAG|ATAAAGAGGG|TTGTTAGGAT|ACATGTGCTA|TTTGAAAGGT|ATTTATAAAA| 2280
|GAAGAGTATA|TTTATTAAAA|TTGCTCAGAA|CATCCAAATT|TCAAGTTTAT|CATTTATCTT| 2340
|ACAATATTTC|AAAAATATTA|AAATAGATAC|ATGAAATACA|GAAGTAAATT|AAAGAGAAAG| 2400

| | | | | | | |
|---|---|---|---|---|---|---|
| TATTTTATTT | TGTAAAAAAA | AATTCTAGGT | TGGACAGGGA | GTACCAGGAA | ACAAAAAACA | 2460 |
| ATGAAAAATG | TGATCTGACA | GAATTATAG | CTCAAAGTAT | AGTAGTCAGT | AATGAAATGG | 2520 |
| CTTAAAAATT | GGCATATAAA | ATGCTAATTA | TAAAATAAAC | AAAATGTAAT | AATACCCTCC | 2580 |
| CTACATGTAA | TGAACTCTGA | GTATTATACT | CTTTTTTGAA | GTCTTGACAA | TGAAAATTTA | 2640 |
| TTTAGACTTT | TATAGACATC | TTGGATAAAG | TAAAACAAAT | TACGAATTAG | CATCCATGAG | 2700 |
| AAAAATATAG | AAAAATTTCT | TAATGTAGTT | TGCAAATCTG | GGGATTGAAG | ATGTGTGTCA | 2760 |
| AGAGATTGTG | ATGGCAGACA | TTTTTTTTCA | GACTATAAAA | TGCACAAACA | ACCATTAAT | 2820 |
| ACATTTTGGT | CAAAAATAGT | ATGTATTTTA | TTTTATGCTA | CAGGAGAGTA | GTCTAAAGTA | 2880 |
| GGACTGGGCA | GAGATCTGAC | ACCCTGGTAA | TCACCGAGAG | ATAGTACACA | GTCTCTGTAG | 2940 |
| AGAAAATAAG | CATAGTGTAT | GATCTCTAAA | ATTATGTGGA | CAAAGGGGAG | ATAACATTAG | 3000 |
| GCATGTGGGG | ATGAAGACTG | AGTACAGAAG | AACAATCTAG | TCAGTCCAAG | AAAACATGTG | 3060 |
| GATCAATGGA | ACAAATAGAA | GAAATGCTAA | AATGAAACAG | AAGTCTTACT | GGAAATAAAA | 3120 |
| GATATGAGGA | AGACAAACAT | TCATGAAAAT | CACTTAGTTT | AGTAGAGAAA | AGATAAAAAT | 3180 |
| AAAGTATTAC | CTTCTTCTTC | ATATACATTG | TTTGATCAGA | TGCCCCTCAA | TAAAACTGAG | 3240 |
| TCTCCAACAG | AACTGAAACT | TTAATATTTT | GTTCACTGCT | CTAATCCCAG | AATCTAAGAC | 3300 |
| ATATCTGGCA | ATAAAAATTA | ATAAATAAAT | ATTTTAATA | AGTAAATCAA | TCACTTAATT | 3360 |
| TTTCTGTAAG | TATCTGTAAC | TTCTCTTCTG | TCTTTCCAAA | AAACACTCAT | AAGTACTGTG | 3420 |
| AATAAGATGA | AAAGAGTGAA | ATAAGATATA | GGCTGTTAGC | TGAAAACATC | TGGATGGCTG | 3480 |
| GCAGTGAAAC | ATTAACTTGA | AATGTAAGAT | TAATGAGTAA | TAGTAAATTT | TAACCTTGGC | 3540 |
| CGTATGATAA | AATGTCTATT | AATATTTTTC | TAAAATACAG | GGCTTTTTGT | TTTTGCCATG | 3600 |
| AGGTTTGCAG | GATCTTGGTT | CCCTGATGAG | GGATCAAACC | TGGGCTCCCC | TGGAAGCACG | 3660 |
| GAGTCTTAGA | TATTTGTATT | ATACACTATC | TTTGGTTTCT | TTTAAAGGGA | AGTAATTCTA | 3720 |
| CTTAAATAAG | AAAATAGATT | GACAAGTAAT | ACACTATTTC | CTCATCTTCC | CATTCCCAGG | 3780 |
| AATTGAGAGC | CATGAAGGTC | CTCATCCTTG | CCTGCCTGGT | GGCTCTGGCC | CTTGCAAGAG | 3840 |
| AGGTAAATAC | AGAAAAAATG | TTGAAATAAA | TAAGACTAGT | ACTATCTGCT | ATGTGTAGAA | 3900 |
| AATTCATTAC | CAACATTGTA | AATGTATAAA | TAATGCACAA | TCTCAGATTT | TTTTTGAATG | 3960 |
| CTAAGAAAGT | CATTTACGTT | CATCCACTAT | CTCAGTAGTA | TCCTATGGGA | CCACAAGTCT | 4020 |
| GAGTCTAGTG | CTTTCTATAG | TATTGTACCA | TCTGTACCAT | CAATCCCTAA | AGAAAAAAGA | 4080 |
| AAATAAACCA | ATAAGCAACA | GACTAACAAG | AAGGAACACA | GATAAGAACA | AAAAGTGAGT | 4140 |
| AATATTGCAT | AAATACAATT | GCATGCATAT | ACAATCTAGA | TAAATATATC | TTATTCCAGT | 4200 |
| GATGAAATAT | TTGTATCCCT | TACTGTAGAG | TGCTAGGTTT | AGCTGTGTCT | ATTCAACACA | 4260 |
| GGATGATACT | CCAGAGGATG | GTATATCAGA | CAACAATAAT | AAATATGTTC | ATAATTATAA | 4320 |
| TAAAAGTGT | TCAGTAAAAA | TTAAAATAAC | TCCTTTTCTG | TTACCCATAA | AAACTCTTCA | 4380 |
| TTAAAGTAAA | ACAAAAATAT | ACTAATGAAA | GTTACTAAAT | TTAAAAGACT | CTCAAAAGAC | 4440 |
| ATATAACATT | TTTATTTTTC | AGATTTGTGA | AATAGATAGC | TCTGAATAAA | GCAAGTAAAA | 4500 |
| ATTAGGTAGG | AAAATATTTA | ATAATGAGTT | GACTGTGGGA | ACTAAAGTGT | TTTTTTTCT | 4560 |
| CTTTAGCTGG | AAGAACTCAA | TGTACCGGTC | GCCACCATGG | GTAAAGGAGA | AGAACTTTTC | 4620 |
| ACTGGAGTTG | TCCCAATTCT | TGTTGAATTA | GATGGTGATG | TTAATGGGCA | CAAATTTTCT | 4680 |
| GTCAGTGGAG | AGGGTGAAGG | TGATGCAACA | TACGGAAAAC | TTACCCTTAA | ATTTATTTGC | 4740 |
| ACTACTGGAA | AACTACCTGT | TCCATGGCCA | ACACTTGTCA | CTACTTTCTC | TTATGGTGTT | 4800 |

```
CAATGCTTTT CAAGATACCC AGATCATATG AAACGGCATG ACTTTTTCAA GAGTGCCATG    4860
CCCGAAGGTT ATGTACAGGA AGAACTATA  TTTTCAAAG  ATGACGGGAA CTACAAGACA    4920
CGTGCTGAAG TCAAGTTTGA AGGTGATACC CTTGTTAATA GAATCGAGTT AAAAGGTATT    4980
GATTTTAAAG AAGATGGAAA CATTCTTGGA CACAAATTGG AATACAACTA TAACTCACAC    5040
AATGTATACA TCATGGCAGA CAAACAAAAG AATGGAATCA AAGTTAACTT CAAAATTAGA    5100
CACAACATTG AAGATGGAAG CGTTCAACTA GCAGACCATT ATCAACAAAA TACTCCAATT    5160
GGCGATGGCC CTGTCCTTTT ACCAGACAAC CATTACCTGT CCACACAATC TGCCCTTTCG    5220
AAAGATCCCA ACGAAAAGAG AGACCACATG GTCCTTCTTG AGTTTGTAAC AGCTGCTGGG    5280
ATTACACATG GCATGGATGA ACTATACAAG TCCGGACTCA GATCTACCAT GCCGCGCTGG    5340
CGTCTGTTCC GCCGTATCGA CCGTGTTGGC AAACAGATCA AACAGGGTAT CCTGCGTGCT    5400
GGCCCGGCTA TCGCTCTGGT TGGCGACGCC CGCGCAGTTG GTTGAGAATT CTGCAGTCGA    5460
CGGTGGATCT AGATAACTGA TCATAATCAG CCATACCACA TTTGTAGAGG TTTTACTTGC    5520
TTTAAAAAAC CTCCCACACC TCCCCCTGAA CCTGAAACAT AAAATGAATG CAATTGTTGT    5580
TGTTAACTTG TTTATTGCAG CTTATAATGG TTACAAATAA AGCAATAGCA TCACAAATTT    5640
CACAAATAAA GCATTTTTTT CACTGCATTC TAGTTGTGGT TTGTCCAAAC TCATCAATGT    5700
ATCTTAACGC GTAAATTGTA AGCGTTAATA TTTTGTTAAA ATTCGCGTTA AATTTTTGTT    5760
AAATCAGCTC ATTTTTTAAC CAATAGGCCG AAATCGGCAA AATCCCTTAT AAATCAAAAG    5820
AATAGACCGA GATAGGGTTG AGTGTTGTTC CAGTTTGGAA CAAGAGTCCA CTATTAAAGA    5880
ACGTGGACTC CAACGTCAAA GGGCGAAAAA CCGTCTATCA GGGCGATGGC CCACTACGTG    5940
AACCATCACC CTAATCAAGT TTTTTGGGGT CGAGGTGCCG TAAAGCACTA AATCGGAACC    6000
CTAAAGGGAG CCCCCGATTT AGAGCTTGAC GGGGAAAGCC GGCGAACGTG GCGAGAAAGG    6060
AAGGGAAGAA AGCGAAAGGA GCGGGCGCTA GGGCGCTGGC AAGTGTAGCG GTCACGCTGC    6120
GCGTAACCAC CACACCCGCC GCGCTTAATG CGCCGCTACA GGGCGCGTCA GGTGGCACTT    6180
TTCGGGGAAA TGTGCGCGGA ACCCCTATTT GTTTATTTTT CTAAATACAT TCAAATATGT    6240
ATCCGCTCAT GAGACAATAA CCCTGATAAA TGCTTCAATA ATATTGAAAA AGGAAGAGTC    6300
CTGAGGCGGA AAGAACCAGC TGTGGAATGT GTGTCAGTTA GGGTGTGGAA AGTCCCCAGG    6360
CTCCCCAGCA GGCAGAAGTA TGCAAAGCAT GCATCTCAAT TAGTCAGCAA CCAGGTGTGG    6420
AAAGTCCCCA GGCTCCCCAG CAGGCAGAAG TATGCAAAGC ATGCATCTCA ATTAGTCAGC    6480
AACCATAGTC CGCCCCTAA  CTCCGCCCAT CCCGCCCCTA ACTCCGCCCA GTTCCGCCCA    6540
TTCTCCGCCC CATGGCTGAC TAATTTTTTT TATTTATGCA GAGGCCGAGG CCGCCTCGGC    6600
CTCTGAGCTA TTCCAGAAGT AGTGAGGAGG CTTTTTTGGA GGCCTAGGCT TTTGCAAAGA    6660
TCGATCAAGA GACAGGATGA GGATCGTTTC GCATGATTGA ACAAGATGGA TTGCACGCAG    6720
GTTCTCCGGC CGCTTGGGTG GAGAGGCTAT TCGGCTATGA CTGGGCACAA CAGACAATCG    6780
GCTGCTCTGA TGCCGCCGTG TTCCGGCTGT CAGCGCAGGG GCGCCCGGTT CTTTTGTCA     6840
AGACCGACCT GTCCGGTGCC CTGAATGAAC TGCAAGACGA GGCAGCGCGG CTATCGTGGC    6900
TGGCCACGAC GGGCGTTCCT TGCGCAGCTG TGCTCGACGT TGTCACTGAA GCGGGAAGGG    6960
ACTGGCTGCT ATTGGGCGAA GTGCCGGGGC AGGATCTCCT GTCATCTCAC CTTGCTCCTG    7020
CCGAGAAAGT ATCCATCATG GCTGATGCAA TGCGGCGGCT GCATACGCTT GATCCGGCTA    7080
CCTGCCCATT CGACCACCAA GCGAAACATC GCATCGAGCG AGCACGTACT CGGATGGAAG    7140
CCGGTCTTGT CGATCAGGAT GATCTGGACG AAGAGCATCA GGGGCTCGCG CCAGCCGAAC    7200
```

```
TGTTCGCCAG GCTCAAGGCG AGCATGCCCG ACGGCGAGGA TCTCGTCGTG ACCCATGGCG     7260
ATGCCTGCTT GCCGAATATC ATGGTGGAAA ATGGCCGCTT TTCTGGATTC ATCGACTGTG     7320
GCCGGCTGGG TGTGGCGGAC CGCTATCAGG ACATAGCGTT GGCTACCCGT GATATTGCTG     7380
AAGAGCTTGG CGGCGAATGG GCTGACCGCT TCCTCGTGCT TTACGGTATC GCCGCTCCCG     7440
ATTCGCAGCG CATCGCCTTC TATCGCCTTC TTGACGAGTT CTTCTGAGCG GGACTCTGGG     7500
GTTCGAAATG ACCGACCAAG CGACGCCCAA CCTGCCATCA CGAGATTTCG ATTCCACCGC     7560
CGCCTTCTAT GAAAGGTTGG GCTTCGGAAT CGTTTTCCGG GACGCCGGCT GGATGATCCT     7620
CCAGCGCGGG GATCTCATGC TGGAGTTCTT CGCCCACCCT AGGGGAGGC TAACTGAAAC      7680
ACGGAAGGAG ACAATACCGG AAGGAACCCG CGCTATGACG GCAATAAAAA GACAGAATAA     7740
AACGCACGGT GTTGGGTCGT TTGTTCATAA ACGCGGGGTT CGGTCCCAGG GCTGGCACTC     7800
TGTCGATACC CCACCGAGAC CCCATTGGGG CCAATACGCC CGCGTTTCTT CCTTTTCCCC    7860
ACCCCACCCC CCAAGTTCGG GTGAAGGCCC AGGGCTCGCA GCCAACGTCG GGCGGCAGG     7920
CCCTGCCATA GCCTCAGGTT ACTCATATAT ACTTTAGATT GATTAAAAC TTCATTTTA      7980
ATTTAAAAGG ATCTAGGTGA AGATCCTTTT TGATAATCTC ATGACCAAAA TCCCTTAACG    8040
TGAGTTTTCG TTCCACTGAG CGTCAGACCC CGTAGAAAAG ATCAAAGGAT CTTCTTGAGA    8100
TCCTTTTTTT CTGCGCGTAA TCTGCTGCTT GCAAACAAAA AAACCACCGC TACCAGCGGT    8160
GGTTTGTTTG CCGGATCAAG AGCTACCAAC TCTTTTTCCG AAGGTAACTG GCTTCAGCAG    8220
AGCGCAGATA CCAAATACTG TCCTTCTAGT GTAGCCGTAG TTAGGCCACC ACTTCAAGAA    8280
CTCTGTAGCA CCGCCTACAT ACCTCGCTCT GCTAATCCTG TTACCAGTGG CTGCTGCCAG    8340
TGGCGATAAG TCGTGTCTTA CCGGGTTGGA CTCAAGACGA TAGTTACCGG ATAAGGCGCA    8400
GCGGTCGGGC TGAACGGGGG GTTCGTGCAC ACAGCCCAGC TTGGAGCGAA CGACCTACAC    8460
CGAACTGAGA TACCTACAGC GTGAGCTATG AGAAAGCGCC ACGCTTCCCG AAGGGAGAAA    8520
GGCGGACAGG TATCCGGTAA GCGGCAGGGT CGGAACAGGA GAGCGCACGA GGGAGCTTCC    8580
AGGGGGAAAC GCCTGGTATC TTTATAGTCC TGTCGGGTTT CGCCACCTCT GACTTGAGCG    8640
TCGATTTTTG TGATGCTCGT CAGGGGGGCG GAGCCTATGG AAAAACGCCA GCAACGCGGC    8700
CTTTTTACGG TTCCTGGCCT TTTGCTGGCC TTTTGCTCAC ATGTTCTTTC CTGCGTTATC    8760
CCCTGATTCT GTGGATAACC GTATTACCGC CATGCAT                              8797
```

( 2 ) INFORMATION FOR SEQ ID NO:7:

( i ) SEQUENCE CHARACTERISTICS:
        ( A ) LENGTH: 22 base pairs
        ( B ) TYPE: nucleic acid
        ( C ) STRANDEDNESS: single
        ( D ) TOPOLOGY: Not Relevant ( i i ) MOLECULE TYPE: other nucleic acid
        ( A ) DESCRIPTION: /desc = "Upstream primer for Bos
            taurus beta casein 5'promoter segment including
            restriction site linker"

( i i i ) HYPOTHETICAL: YES ( x i ) SEQUENCE DESCRIPTION: SEQ ID NO:7:

```
GGTGAGAGAC GTCATTAGGA AA                                              22
```

( 2 ) INFORMATION FOR SEQ ID NO:8:

( i ) SEQUENCE CHARACTERISTICS:
        ( A ) LENGTH: 26 base pairs (B) TYPE: nucleic acid
(C) STRANDEDNESS: single
(D) TOPOLOGY: Not Relevant (i i) MOLECULE TYPE: other nucleic acid
(A) DESCRIPTION: /desc = "Downstream primer for Bos taurus beta casein 5'regulatory region including restriction site linker"

(i i i) HYPOTHETICAL: YES (x i) SEQUENCE DESCRIPTION: SEQ ID NO:8:

TTACCTCACC GGTACTACAT TGAGTT    26

(2) INFORMATION FOR SEQ ID NO:9:

(i) SEQUENCE CHARACTERISTICS:
(A) LENGTH: 31 base pairs
(B) TYPE: nucleic acid
(C) STRANDEDNESS: single
(D) TOPOLOGY: Not Relevant (i i) MOLECULE TYPE: other nucleic acid
(A) DESCRIPTION: /desc = "Upstream primer for Bos taurus beta casein 3'regulatory segment including restriction site linker"

(i i i) HYPOTHETICAL: YES (x i) SEQUENCE DESCRIPTION: SEQ ID NO:9:

CCAGGATGGG TACCAGGATA AAATCCACCC C    31

(2) INFORMATION FOR SEQ ID NO:10:

(i) SEQUENCE CHARACTERISTICS:
(A) LENGTH: 34 base pairs
(B) TYPE: nucleic acid
(C) STRANDEDNESS: single
(D) TOPOLOGY: Not Relevant (i i) MOLECULE TYPE: other nucleic acid
(A) DESCRIPTION: /desc = "Downstream primer for Bos taurus beta casein 3'regulatory region including restriction site linker"

(i i i) HYPOTHETICAL: YES (x i) SEQUENCE DESCRIPTION: SEQ ID NO:10:

GGGAATTGGA TCCAATTTTA ATTTTCCACA GCTC    34

(2) INFORMATION FOR SEQ ID NO:11:

(i) SEQUENCE CHARACTERISTICS:
(A) LENGTH: 40 base pairs
(B) TYPE: nucleic acid
(C) STRANDEDNESS: single
(D) TOPOLOGY: Not Relevant (i i) MOLECULE TYPE: other nucleic acid
(A) DESCRIPTION: /desc = "Upstream primer for Bos taurus alpha-S1-casein 5'promoter region including restriction site linker"

(i i i) HYPOTHETICAL: YES (x i) SEQUENCE DESCRIPTION: SEQ ID NO:11:

GGCCGACGTC CCAACCCAGA TGGGCATGAA AAAGGAGAGA    40

(2) INFORMATION FOR SEQ ID NO:12:

(i) SEQUENCE CHARACTERISTICS:
(A) LENGTH: 39 base pairs ( B ) TYPE: nucleic acid
            ( C ) STRANDEDNESS: single
            ( D ) TOPOLOGY: Not Relevant ( i i ) MOLECULE TYPE: other nucleic acid
            ( A ) DESCRIPTION: /desc = "Downstream primer for Bos
                taurus alpha-S1-casein 5'regulatory region including
                restriction site linker"

( i i i ) HYPOTHETICAL: YES ( x i ) SEQUENCE DESCRIPTION: SEQ ID NO:12:

GGCCGCTAGC AGCAACAGCC ACAAGACAGG TAAGGATGA 39

( 2 ) INFORMATION FOR SEQ ID NO:13:

( i ) SEQUENCE CHARACTERISTICS:
            ( A ) LENGTH: 40 base pairs
            ( B ) TYPE: nucleic acid
            ( C ) STRANDEDNESS: single
            ( D ) TOPOLOGY: Not Relevant ( i i ) MOLECULE TYPE: other nucleic acid
            ( A ) DESCRIPTION: /desc = "Upstream primer for Bos
                taurus alpha-S1-casein 3'regulatory region including
                restriction site linker"

( i i i ) HYPOTHETICAL: YES ( x i ) SEQUENCE DESCRIPTION: SEQ ID NO:13:

GGCCGTCGAC CTGAGGGACT CCACAGTTAT GGTCTTTGGT 40

( 2 ) INFORMATION FOR SEQ ID NO:14:

( i ) SEQUENCE CHARACTERISTICS:
            ( A ) LENGTH: 40 base pairs
            ( B ) TYPE: nucleic acid
            ( C ) STRANDEDNESS: single
            ( D ) TOPOLOGY: Not Relevant ( i i ) MOLECULE TYPE: other nucleic acid
            ( A ) DESCRIPTION: /desc = "Downstream primer for Bos
                taurus alpha S1 casein 3'regulatory region including
                restriction site linker"

( i i i ) HYPOTHETICAL: YES ( x i ) SEQUENCE DESCRIPTION: SEQ ID NO:14:

GGCCGGGCCC GGGATTGCAT TGAATCTATA ATTGCTTGG 40

( 2 ) INFORMATION FOR SEQ ID NO:15:

( i ) SEQUENCE CHARACTERISTICS:
            ( A ) LENGTH: 40 base pairs
            ( B ) TYPE: nucleic acid
            ( C ) STRANDEDNESS: single
            ( D ) TOPOLOGY: Not Relevant ( i i ) MOLECULE TYPE: other nucleic acid
            ( A ) DESCRIPTION: /desc = "Upstream primer for Capra
                hircus beta lactoglobulin 5'regulatory region including
                restriction site linker"

( i i i ) HYPOTHETICAL: YES ( x i ) SEQUENCE DESCRIPTION: SEQ ID NO:15:

GGCCGCTAGC CCAACCCAGA TGGGCATGAA AAAGGAGAGA 40

( 2 ) INFORMATION FOR SEQ ID NO:16:

( i ) SEQUENCE CHARACTERISTICS:
            ( A ) LENGTH: 38 base pairs ( B ) TYPE: nucleic acid
( C ) STRANDEDNESS: single
( D ) TOPOLOGY: Not Relevant ( i i ) MOLECULE TYPE: other nucleic acid
( A ) DESCRIPTION: /desc = "Downstream primer for Capra
hircus beta lactoglobulin 5'promoter region including
restriction site linker"

( i i i ) HYPOTHETICAL: YES ( x i ) SEQUENCE DESCRIPTION: SEQ ID NO:16:

GGCCACCGGT GCAACAGCCA CAAGACAGGT AAGGATGA                    38

( 2 ) INFORMATION FOR SEQ ID NO:17:

( i ) SEQUENCE CHARACTERISTICS:
( A ) LENGTH: 40 base pairs
( B ) TYPE: nucleic acid
( C ) STRANDEDNESS: single
( D ) TOPOLOGY: Not Relevant ( i i ) MOLECULE TYPE: other nucleic acid
( A ) DESCRIPTION: /desc = "Upstream primer for Capra
hircus beta lactoglobulin 3'regulatory region including
restriction site linker"

( i i i ) HYPOTHETICAL: YES ( x i ) SEQUENCE DESCRIPTION: SEQ ID NO:17:

GGCCGTCGAC GGCCTGGAGA AATTCGACAA AGCCCTCAAG                  40

( 2 ) INFORMATION FOR SEQ ID NO:18:

( i ) SEQUENCE CHARACTERISTICS:
( A ) LENGTH: 40 base pairs
( B ) TYPE: nucleic acid
( C ) STRANDEDNESS: single
( D ) TOPOLOGY: Not Relevant ( i i ) MOLECULE TYPE: other nucleic acid
( A ) DESCRIPTION: /desc = "Downstream primer for Capra
hircus beta lactoglobulin 3'regulatory region including
restriction site linker"

( i i i ) HYPOTHETICAL: YES ( x i ) SEQUENCE DESCRIPTION: SEQ ID NO:18:

GGCCGGATTC TCCACCCAAA CCCATGTCCA TTGTGTCAGT                  40

( 2 ) INFORMATION FOR SEQ ID NO:19:

( i ) SEQUENCE CHARACTERISTICS:
( A ) LENGTH: 23 amino acids
( B ) TYPE: amino acid
( C ) STRANDEDNESS: Not Relevant
( D ) TOPOLOGY: Not Relevant ( i i ) MOLECULE TYPE: peptide ( i i i ) HYPOTHETICAL: YES ( i v ) ANTI-SENSE: NO ( x i ) SEQUENCE DESCRIPTION: SEQ ID NO:19:

Phe Ala Leu Ala Leu Lys Ala Leu Lys Lys Ala Leu Lys Lys Leu Lys
 1               5                  10                   15

Lys Ala Leu Lys Lys Ala Leu
             20

( 2 ) INFORMATION FOR SEQ ID NO:20:

( i ) SEQUENCE CHARACTERISTICS:
  ( A ) LENGTH: 31 amino acids
  ( B ) TYPE: amino acid
  ( C ) STRANDEDNESS: Not Relevant
  ( D ) TOPOLOGY: Not Relevant ( i i ) MOLECULE TYPE: peptide ( i i i ) HYPOTHETICAL: YES ( i v ) ANTI-SENSE: NO ( x i ) SEQUENCE DESCRIPTION: SEQ ID NO:20:

```
Phe Ala Lys Leu Ala Leu Ala Lys Leu Ala Leu Ala Leu Lys Ala Leu
 1               5                  10                  15
Lys Lys Ala Leu Lys Lys Leu Lys Lys Ala Leu Lys Lys Ala Leu
        20                  25                  30
```

( 2 ) INFORMATION FOR SEQ ID NO:21:

( i ) SEQUENCE CHARACTERISTICS:
  ( A ) LENGTH: 38 amino acids
  ( B ) TYPE: amino acid
  ( C ) STRANDEDNESS: Not Relevant
  ( D ) TOPOLOGY: Not Relevant ( i i ) MOLECULE TYPE: peptide ( i i i ) HYPOTHETICAL: YES ( x i ) SEQUENCE DESCRIPTION: SEQ ID NO:21:

```
Phe Ala Leu Ala Lys Leu Ala Leu Ala Lys Leu Ala Leu Ala Lys Leu
 1               5                  10                  15
Ala Leu Ala Leu Lys Ala Leu Lys Lys Ala Leu Lys Lys Leu Lys Lys
        20                  25                  30
Ala Leu Lys Lys Ala Leu
        35
```

( 2 ) INFORMATION FOR SEQ ID NO:22:

( i ) SEQUENCE CHARACTERISTICS:
  ( A ) LENGTH: 38 amino acids
  ( B ) TYPE: amino acid
  ( C ) STRANDEDNESS: Not Relevant
  ( D ) TOPOLOGY: Not Relevant ( i i ) MOLECULE TYPE: peptide ( i i i ) HYPOTHETICAL: YES ( x i ) SEQUENCE DESCRIPTION: SEQ ID NO:22:

```
Met Pro Arg Trp Arg Leu Phe Arg Arg Ile Asp Arg Val Gly Lys Gln
 1               5                  10                  15
Ile Lys Gln Gly Ile Leu Arg Ala Gly Pro Ala Ile Ala Leu Val Gly
        20                  25                  30
Asp Ala Arg Ala Leu Gly
        35
```

( 2 ) INFORMATION FOR SEQ ID NO:23:

( i ) SEQUENCE CHARACTERISTICS:
  ( A ) LENGTH: 38 amino acids
  ( B ) TYPE: amino acid
  ( C ) STRANDEDNESS:
  ( D ) TOPOLOGY: Not Relevant ( i i ) MOLECULE TYPE: peptide ( i i i ) HYPOTHETICAL: YES ( x i ) SEQUENCE DESCRIPTION: SEQ ID NO:23:

Leu Ala Lys Lys Leu Ala Lys Lys Leu Lys Lys Leu Ala Lys Lys Leu
1               5                   10                  15

Ala Lys Leu Ala Leu Ala Leu Lys Ala Leu Ala Leu Lys Ala Leu Ala
            20                  25                  30

Leu Lys Ala Leu Ala Leu
        35

( 2 ) INFORMATION FOR SEQ ID NO:24:

( i ) SEQUENCE CHARACTERISTICS:
       ( A ) LENGTH: 38 amino acids
       ( B ) TYPE: amino acid
       ( C ) STRANDEDNESS:
       ( D ) TOPOLOGY: Not Relevant ( i i ) MOLECULE TYPE: peptide ( i i i ) HYPOTHETICAL: YES ( x i ) SEQUENCE DESCRIPTION: SEQ ID NO:24:

Met Pro Lys Trp Lys Val Phe Lys Lys Ile Glu Lys Val Gly Arg Asn
1               5                   10                  15

Ile Arg Asn Gly Ile Val Lys Ala Gly Pro Ala Ile Ala Val Leu Gly
            20                  25                  30

Glu Ala Lys Ala Leu Gly
        35

( 2 ) INFORMATION FOR SEQ ID NO:25:

( i ) SEQUENCE CHARACTERISTICS:
       ( A ) LENGTH: 30 amino acids
       ( B ) TYPE: amino acid
       ( C ) STRANDEDNESS:
       ( D ) TOPOLOGY: Not Relevant ( i i ) MOLECULE TYPE: peptide ( i i i ) HYPOTHETICAL: YES ( x i ) SEQUENCE DESCRIPTION: SEQ ID NO:25:

Met Lys Arg Met Val Ser Trp Ser Phe His Lys Leu Lys Thr Met Lys
1               5                   10                  15

His Leu Leu Leu Leu Leu Leu Cys Val Phe Leu Val Lys Ser
            20                  25                  30

( 2 ) INFORMATION FOR SEQ ID NO:26:

( i ) SEQUENCE CHARACTERISTICS:
       ( A ) LENGTH: 31 amino acids
       ( B ) TYPE: amino acid
       ( C ) STRANDEDNESS:
       ( D ) TOPOLOGY: Not Relevant ( i i ) MOLECULE TYPE: peptide ( i i i ) HYPOTHETICAL: YES ( x i ) SEQUENCE DESCRIPTION: SEQ ID NO:26:

Leu Ala Lys Lys Leu Ala Lys Lys Leu Lys Lys Leu Ala Lys Lys Leu
1               5                   10                  15

Ala Lys Leu Ala Leu Ala Leu Lys Ala Leu Ala Leu Lys Ala Leu
            20                  25                  30

(2) INFORMATION FOR SEQ ID NO:27:

(i) SEQUENCE CHARACTERISTICS:
        (A) LENGTH: 23 amino acids
        (B) TYPE: amino acid
        (C) STRANDEDNESS:
        (D) TOPOLOGY: Not Relevant (ii) MOLECULE TYPE: peptide (iii) HYPOTHETICAL: YES (xi) SEQUENCE DESCRIPTION: SEQ ID NO:27:

```
Phe Leu Lys Lys Leu Ala Lys Lys Leu Lys Lys Leu Ala Lys Lys Leu
 1               5                  10                  15
Ala Lys Leu Ala Lys Lys Leu
            20
```

(2) INFORMATION FOR SEQ ID NO:28:

(i) SEQUENCE CHARACTERISTICS:
        (A) LENGTH: 23 amino acids
        (B) TYPE: amino acid
        (C) STRANDEDNESS:
        (D) TOPOLOGY: Not Relevant (ii) MOLECULE TYPE: peptide (iii) HYPOTHETICAL: YES (xi) SEQUENCE DESCRIPTION: SEQ ID NO:28:

```
Leu Ala Lys Lys Leu Ala Lys Lys Leu Lys Lys Leu Ala Lys Lys Leu
 1               5                  10                  15
Ala Lys Leu Ala Lys Lys Leu
            20
```

(2) INFORMATION FOR SEQ ID NO:29:

(i) SEQUENCE CHARACTERISTICS:
        (A) LENGTH: 31 amino acids
        (B) TYPE: amino acid
        (C) STRANDEDNESS:
        (D) TOPOLOGY: Not Relevant (ii) MOLECULE TYPE: peptide (iii) HYPOTHETICAL: YES (xi) SEQUENCE DESCRIPTION: SEQ ID NO:29:

```
Leu Ala Lys Leu Ala Leu Ala Lys Leu Ala Leu Ala Leu Lys Ala Leu
 1               5                  10                  15
Lys Lys Ala Leu Lys Lys Leu Lys Lys Ala Leu Lys Lys Ala Leu
                20              25                  30
```

(2) INFORMATION FOR SEQ ID NO:30:

(i) SEQUENCE CHARACTERISTICS:
        (A) LENGTH: 30 amino acids
        (B) TYPE: amino acid
        (C) STRANDEDNESS:
        (D) TOPOLOGY: Not Relevant (ii) MOLECULE TYPE: peptide (iii) HYPOTHETICAL: YES (xi) SEQUENCE DESCRIPTION: SEQ ID NO:30:

```
Met Lys Arg Met Val Ser Trp Ser Phe Lys Lys Leu Lys Thr Met Lys
 1               5                  10                  15
```

```
Lys  Leu  Leu  Leu  Leu  Leu  Leu  Cys  Val  Phe  Leu  Val  Lys  Ser
               20                     25                     30
```

(2) INFORMATION FOR SEQ ID NO:31:

(i) SEQUENCE CHARACTERISTICS:
        (A) LENGTH: 20 base pairs
        (B) TYPE: nucleic acid
        (C) STRANDEDNESS: Not Relevant
        (D) TOPOLOGY: Not Relevant (ii) MOLECULE TYPE: other nucleic acid
        (A) DESCRIPTION: /desc = "Primer for Bos taurus beta casein 5'flanking segment"

(iii) HYPOTHETICAL: YES (xi) SEQUENCE DESCRIPTION: SEQ ID NO:31:

```
GCCTTTATGG CTGAGGTATG                                          20
```

(2) INFORMATION FOR SEQ ID NO:32:

(i) SEQUENCE CHARACTERISTICS:
        (A) LENGTH: 21 base pairs
        (B) TYPE: nucleic acid
        (C) STRANDEDNESS: Not Relevant
        (D) TOPOLOGY: Not Relevant (ii) MOLECULE TYPE: other nucleic acid
        (A) DESCRIPTION: /desc = "Primer for Bos taurus beta casein 5'flanking region"

(iii) HYPOTHETICAL: YES (xi) SEQUENCE DESCRIPTION: SEQ ID NO:32:

```
CATCTATCTG TCCCAAAGCT G                                        21
```